(12) United States Patent
Jansen

(10) Patent No.: US 9,566,151 B2
(45) Date of Patent: Feb. 14, 2017

(54) PERCUTANEOUSLY IMPLANTABLE FLAP STENT, DEVICE FOR APPLYING THE SAME AND METHOD FOR PRODUCING THE FLAP STENT

(75) Inventor: Josef Jansen, Bergisch Gladbach (DE)

(73) Assignee: BE INNOVATIVE GMBH, Köln (DE)

( * ) Notice: Subject to any disclaimer, the term of this patent is extended or adjusted under 35 U.S.C. 154(b) by 265 days.

(21) Appl. No.: 13/379,362

(22) PCT Filed: Jun. 24, 2010

(86) PCT No.: PCT/DE2010/000729
§ 371 (c)(1),
(2), (4) Date: Dec. 20, 2011

(87) PCT Pub. No.: WO2011/000354
PCT Pub. Date: Jan. 6, 2011

(65) Prior Publication Data
US 2012/0101567 A1    Apr. 26, 2012

(30) Foreign Application Priority Data

Jun. 29, 2009 (DE) .................. 10 2009 031 173
Aug. 17, 2009 (DE) .................. 10 2009 037 739

(51) Int. Cl.
*A61F 2/24* (2006.01)
*A61F 2/30* (2006.01)
(Continued)

(52) U.S. Cl.
CPC .............. *A61F 2/24* (2013.01); *A61F 2/2412* (2013.01); *A61F 2/2418* (2013.01); *A61F 2/2436* (2013.01); *A61F 2/2475* (2013.01); *A61F 2002/30329* (2013.01); *A61F 2002/8483* (2013.01); *A61F 2002/8486* (2013.01); *A61F 2002/9522* (2013.01); *A61F 2220/005* (2013.01);
(Continued)

(58) Field of Classification Search
CPC ........ A61F 2/24; A61F 2/2409; A61F 2/2418; A61F 2/2475; A61F 2250/0036; A61F 2220/0016; A61F 2/2412
USPC ..................... 623/1.24, 1.26, 1.36, 2.1, 2.14, 2.15,623/2.16, 2.17, 2.18, 2.19
See application file for complete search history.

(56) References Cited

U.S. PATENT DOCUMENTS 6,168,616 B1    1/2001  Brown, III
6,251,135 B1 *  6/2001  Stinson et al. ............... 623/1.34
(Continued)

FOREIGN PATENT DOCUMENTS

DE       10050092 A1   4/2002
DE       10050305 A1   4/2002
(Continued)

*Primary Examiner* — David Isabella
*Assistant Examiner* — Suba Ganesan
(74) *Attorney, Agent, or Firm* — McGlew and Tuttle, P.C.

(57) ABSTRACT

A valve stent includes a plurality of crown elements arranged coaxially one behind the other, each formed by several u-shaped bends with at least one base and two ends. The bases of one crown element are connected to the ends of another crown element via connection bars. To produce this valve stent, 3D droplet dosing technology is used to form a thin-walled sandwich structure. A device, suitable for application of a stent is provided with positioning wires having clamps at their ends which can be connected to the fixing hooks at the ends of the crown elements in force-locking manner.

39 Claims, 11 Drawing Sheets

(51) Int. Cl.
*A61F 2/848* (2013.01)
*A61F 2/95* (2013.01)

(52) U.S. Cl.
CPC .............. *A61F 2220/0008* (2013.01); *A61F 2220/0025* (2013.01); *A61F 2230/0054* (2013.01); *A61F 2250/006* (2013.01)

(56) References Cited

U.S. PATENT DOCUMENTS

| | | | |
|---|---|---|---|
| 8,728,154 B2* | 5/2014 | Alkhatib | 623/2.17 |
| 2002/0032481 A1* | 3/2002 | Gabbay | 623/2.11 |
| 2003/0236568 A1 | 12/2003 | Hojeibane et al. | |
| 2005/0203605 A1* | 9/2005 | Dolan | A61F 2/2418 |
| | | | 623/1.11 |
| 2006/0235509 A1 | 10/2006 | Lafontaine | |
| 2006/0259137 A1 | 11/2006 | Artof et al. | |
| 2006/0265056 A1 | 11/2006 | Nguyen et al. | |
| 2006/0282157 A1* | 12/2006 | Hill et al. | 623/1.24 |
| 2008/0255660 A1* | 10/2008 | Guyenot | A61F 2/2418 |
| | | | 623/2.14 |

FOREIGN PATENT DOCUMENTS

| | | |
|---|---|---|
| DE | 101 21 210 B4 | 11/2005 |
| DE | 202007005491 U1 | 6/2007 |
| EP | 2 047 824 A1 | 4/2009 |
| WO | 2007/097983 A2 | 8/2007 |
| WO | 2008/029296 A2 | 3/2008 |
| WO | 2009/045334 A1 | 4/2009 |

* cited by examiner

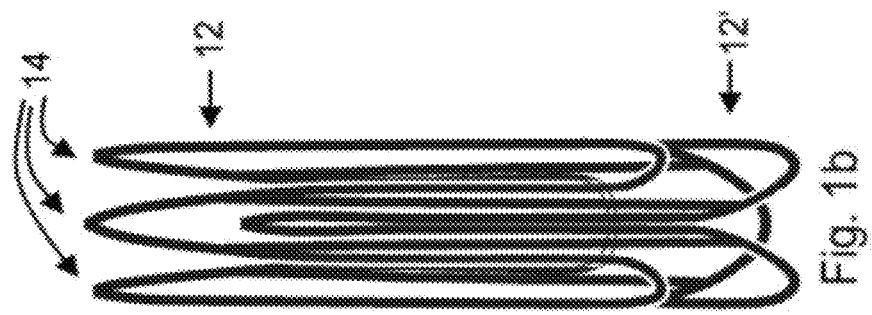
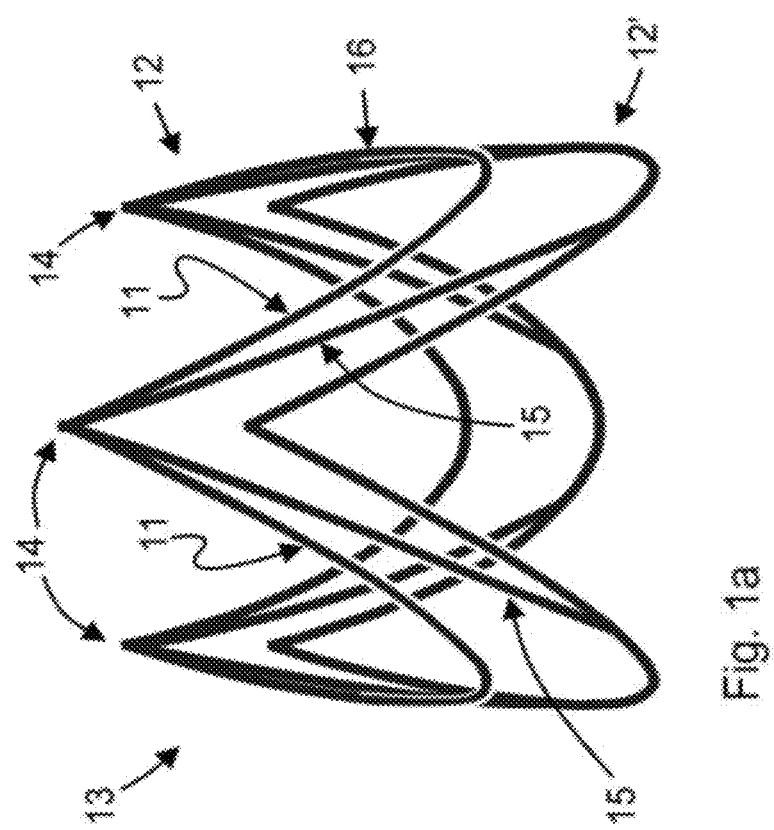

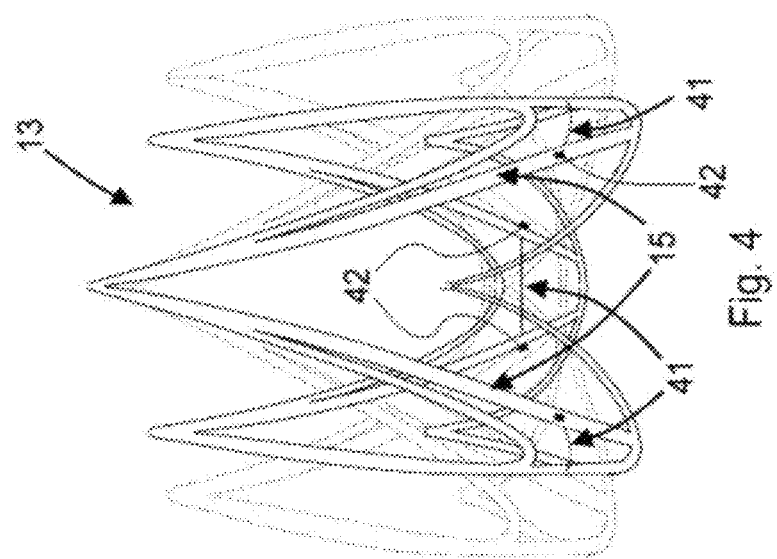
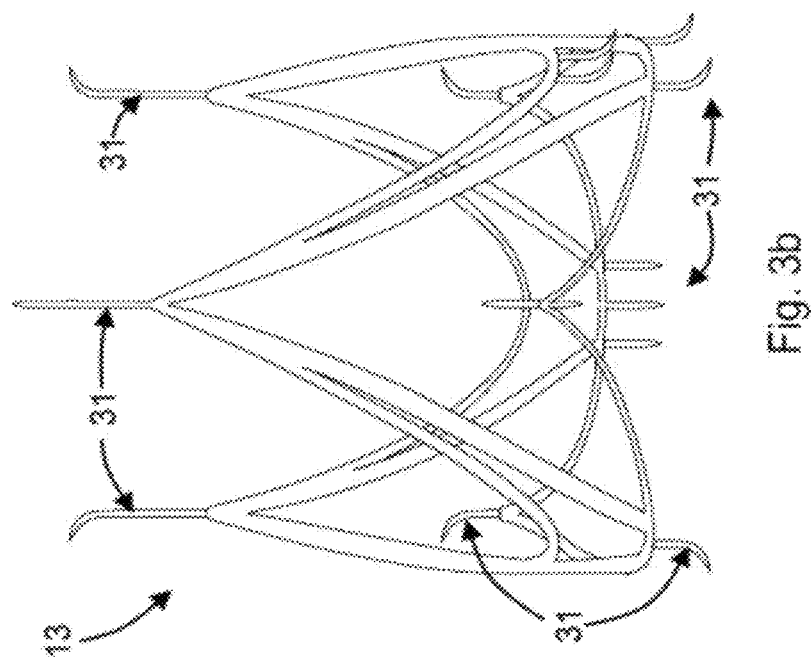

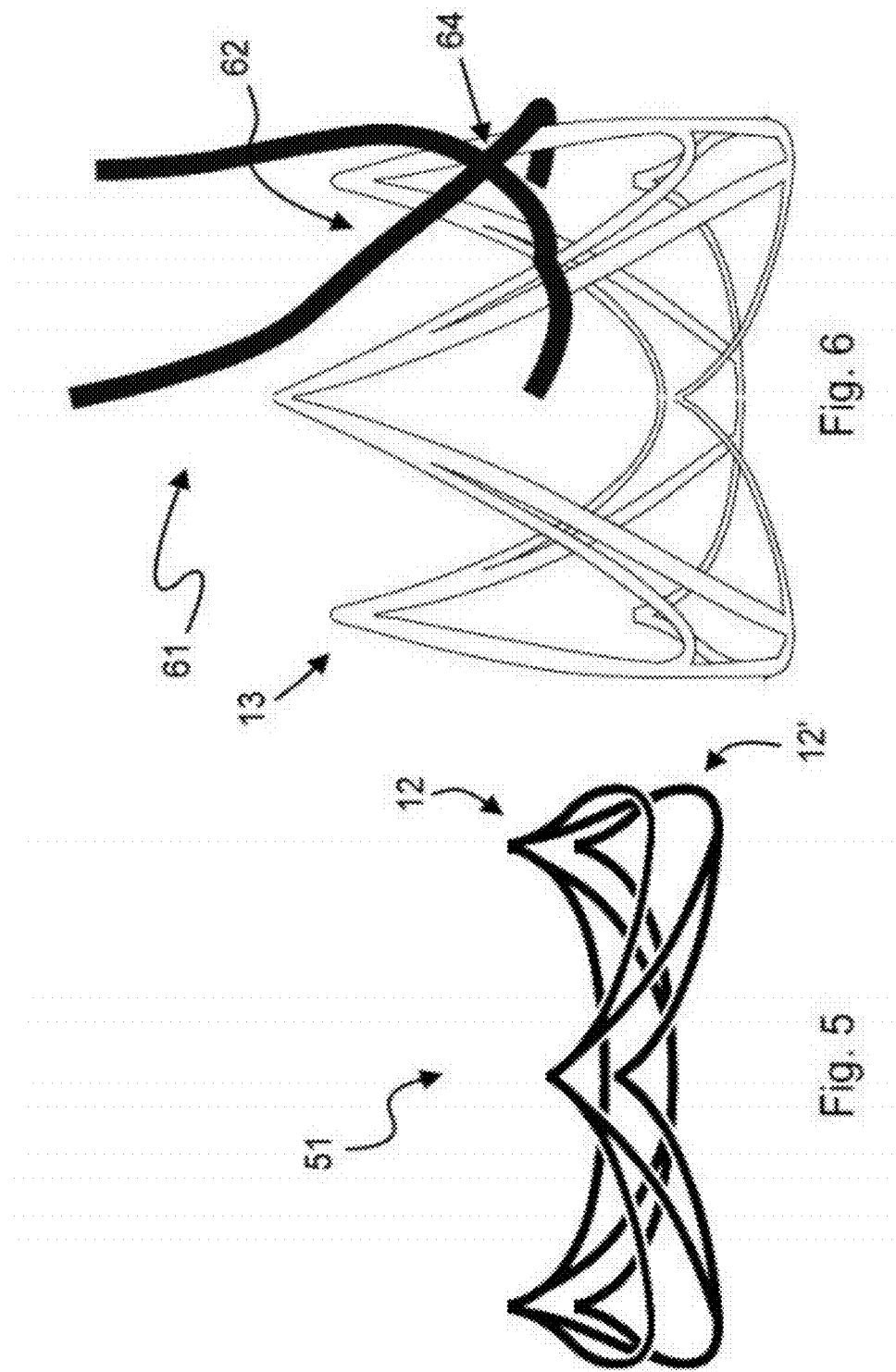

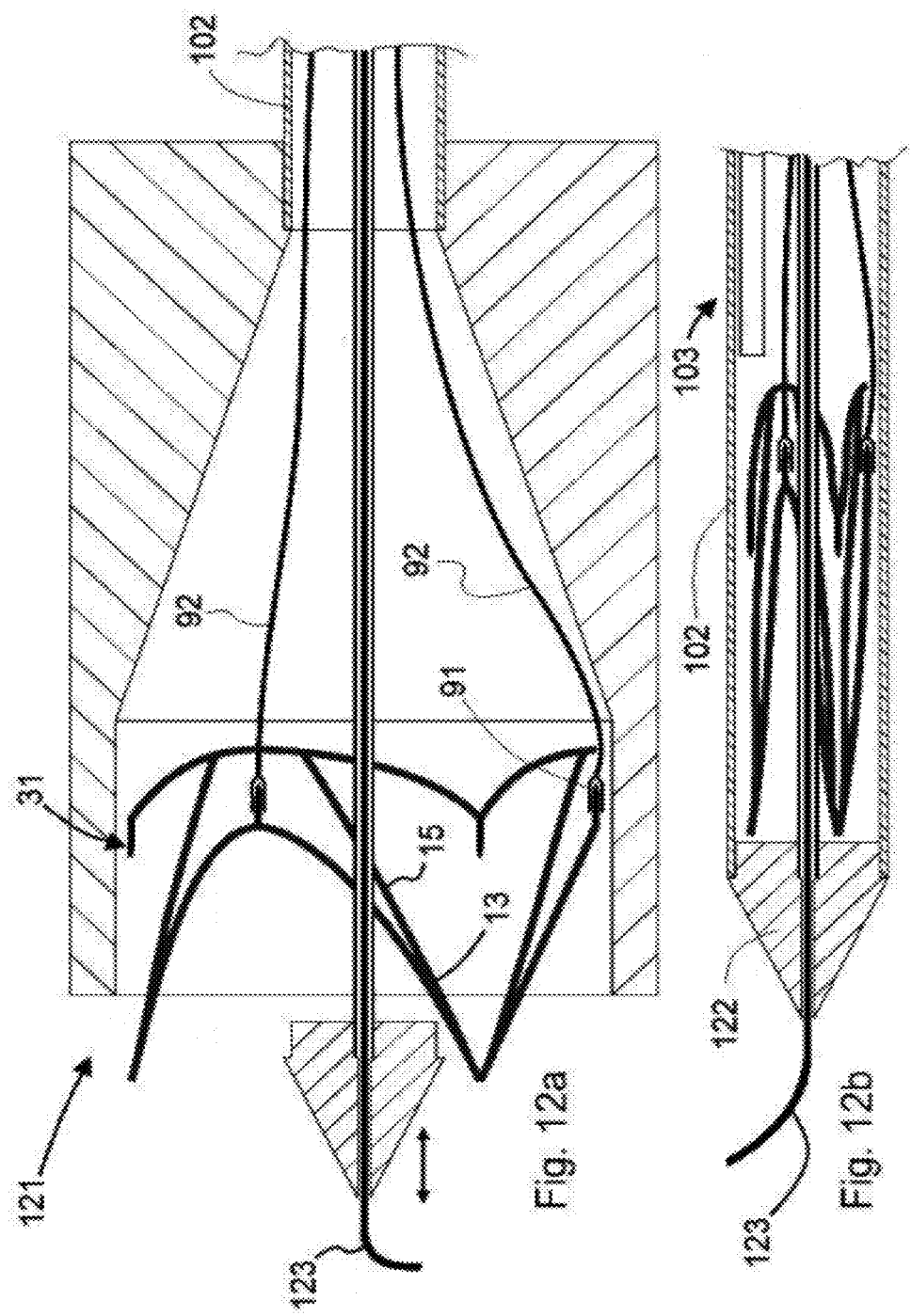

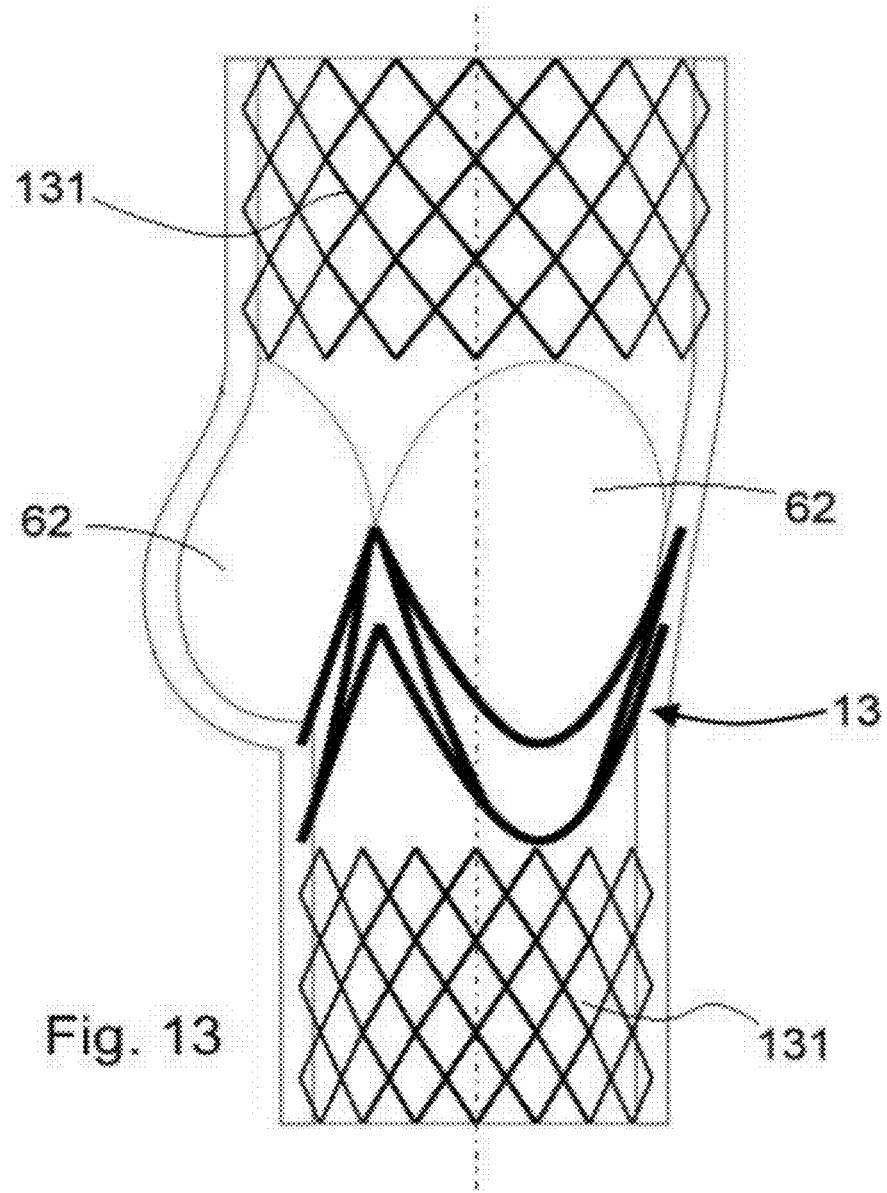

PERCUTANEOUSLY IMPLANTABLE FLAP STENT, DEVICE FOR APPLYING THE SAME AND METHOD FOR PRODUCING THE FLAP STENT

CROSS REFERENCE TO RELATED APPLICATIONS

This application is a United States National Phase application of International Application PCT/DE2010/000729 and claims the benefit of priority under 35 U.S.C. §119 of German Patent Application DE 10 2009 031 173.4 filed Jun. 29, 2009, German Patent Application DE 10 2009 037 739.5 filed Aug. 17, 2009, the entire contents of which are incorporated herein by reference.

FIELD OF THE INVENTION

The present invention relates to a valve stent composed of a plurality of crown elements that are arranged coaxially one behind the other and each formed by several u-shaped bends with at least one base and two ends.
Furthermore, the present invention relates to a device for the application of a stent as well as the process for making a valve stent to take up polymeric valve leaflets

BACKGROUND OF THE INVENTION

Surgical heart valve replacement is usually carried out on a cardioplegic (arrested) heart. The affected heart valve is cut out and the heart valve prosthesis to be implanted is stitched in. This complicated procedure is carried out with the aid of heart-lung machines and is to some extent not an option for high-risk patients. Thus, a minimally invasive or percutaneous method to replace a heart valve is sought after, so that this cardiosurgical intervention can routinely be offered to a broad group of patients in the long-term.

Depending on the anatomical and physiological condition of the patient (e.g. condition of the femoral arteries), two implantation methods are available for the physician—transfemoral implantation (via the groins) and transapical implantation (via the cardiac apex). Each strategy requires a respective adapted application device since the valve stent one case is ejected against flow direction (retrograde) and in the other case with flow direction (anterograde). During the implantation process, the valve prosthesis must be easily maneuverable through the access vessels and at the implantation site to ensure optimal position accuracy. Furthermore, the prosthesis must be able to be securely anchored. Amongst other things, a certain excess in the diameter of the valve prosthesis compared to the blood vessel is generally used in order to generate a radial pressure on the blood vessel by the prosthesis.

These percutaneous applicable valve systems consist of a valve-carrying stent, additional fixing elements connected to this stent (and, if necessary, further structures) to anchor the heart valves in the heart and in the vessel of the patient and an application device (or catheter system) for minimally invasive introduction and positioning of the heart valve at the implantation site in the patient.

In principle, such systems can also be used to replace defective venous valves or to relieve them by connecting them in series with an artificial venous valve. Unlike heart valve prosthesis, venous valve prosthesis can also be implanted heterotopically (not orthotopically), i.e. not at the same place as the body's own venous valve.

Usually, conventional stent designs are similar to an enlarged but valve-carrying coronary stent or a stent with sawtooth-, diamond- or meander-shaped netlike braid to brace vasoconstrictions. The stents are thereby formed as self-expanding or not self-expanding, foldable structures often without special fixing systems. However, these stents are not or only insufficiently adapted to the biomechanics and anatomy of highly stressed heart- or venous valve prostheses.

Another stent is disclosed in DE 20 2007 005491 U1. The medical device described therein serves for treatment of aortic valve insufficiency using a self-expandable endoprosthesis that can be introduced minimally invasively into the patient's body to position and fix a heart valve prosthesis in the aorta of the patient, wherein the endoprosthesis has at least three position brackets for independent positioning of the medical device in the aorta of the patient and one retaining segment with retaining brackets to take up a heart valve prosthesis, and wherein, during introduction of the medical device into the body of the patient, the endoprosthesis has a shaping that can be defined in advance, wherein the medical device has a folded state in the initial shaping of the endoprosthesis and an expanded state in the second shaping of the endoprosthesis. It is also provided that the endoprosthesis is in one piece with a structure cut from a metal tube in which any position bracket is assigned to one retaining bracket and in which, at the distal end of the endoprosthesis, any end portion of the respective position bracket is connected to the associated retaining bracket.

Shape memory materials are used for the self-expanding valve-carrying stent systems and, if necessary, for additional anchor and fixing elements. These can be shape memory polymers or memory metals, such as copper/zinc/aluminium-, copper/aluminium/nickel or nickel/titanium ("nitinol") shape memory alloys. In particular, shape memory materials with one-way effect are used, where the alloy only returns to the former shape when the critical temperature or the shape transformation temperature is exceeded and retains this shape even if the temperature once again falls below the critical temperature. Memory metals are usually chosen such that the critical temperature is below the body temperature, so that the expansion into the final shape is evoked at body temperature, i.e. during introduction of the valve prosthesis into the patient. The non-self-expanding, valve-carrying stents are mostly made of stainless steel alloys, such as 316 L. Spring steel, such as Phynax/Elgiloy or high strength polymers or plastics, such as PEEK, polyurethane and fibre- or nano-reinforced polyurethanes, are also suitable for valve, bulb or anchoring stents, as well as for vascular stents and stent grafts. Alternatively, they can also be made of bio-resorbing materials, for example based on magnesium alloys or bio-resorbable plastics (such as polylactate or other specific polyurethanes).

The previously described stents are disadvantageous as a result of their stiffness under forces directed radially inwards. Although it is possible in principle to increase the stiffness of a stent using more supporting material, this results in an adverse increase of the area of extraneous material within the blood vessels. This increases the risk of thrombotic accumulations, for example.

SUMMARY OF THE INVENTION

It is therefore a task of the present invention to create a valve stent designed in such a way that it has maximum stiffness with minimum use of materials.

According to the invention, it is intended that the bases of a crown element are connected to the ends of another crown element by connection bars. In contrast to the stent designs in the prior art, the valve stent according to the invention is not integrated into the usual mesh-like wireframe, but is optimally constructed for the anatomy and biomechanics of heart or venous valves, resulting in particular from the increased stiffness of the stent structure according to the invention.

Advantageous designs of the present invention are described in the following as well as in claims. For this, the specific formations shown in the figures are referred to. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1a is a view of a valve stent according to the invention;

FIG. 1b is a view of the valve stent of FIG. 1b, that has been folded down to a very small diameter;

FIG. 3b is a view of a is a valve stent according to the invention in which the crown elements are not parallel to each other;

FIG. 4 is a view of a is a valve stent according to the invention in which the crown elements are not parallel to each other, shown in a completely folded state with solid lines and a completely unfolded state with dotted lines;

FIG. 5 is a view of a separate anchoring stent having at least one or more than one crown element;

FIG. 6 is a view of a bulb stent;

FIG. 9a is a perspective view showing self-opening clamps laid around bent claws or fixing hooks FIG. 9b is a view of a fixing hook with attached clamp taken from the perspective of line AA of FIG. 3a;

FIG. 12a is a sectional view showing an additional funnel-shaped device attachable around the lock 102, that can be used to load the valve stent as well as the anchoring stent or the bulb stent in the operating room before application;

FIG. 12b is sectional view showing stents located within the lock of a catheter with the lock head closed; and FIG. 13 is a view showing a valve stent as well as additional wire frames, located proximal to the valve stent and distal to the bulbs, which are integrated into a conduit.

DESCRIPTION OF THE PREFERRED EMBODIMENTS

Figure 3A:
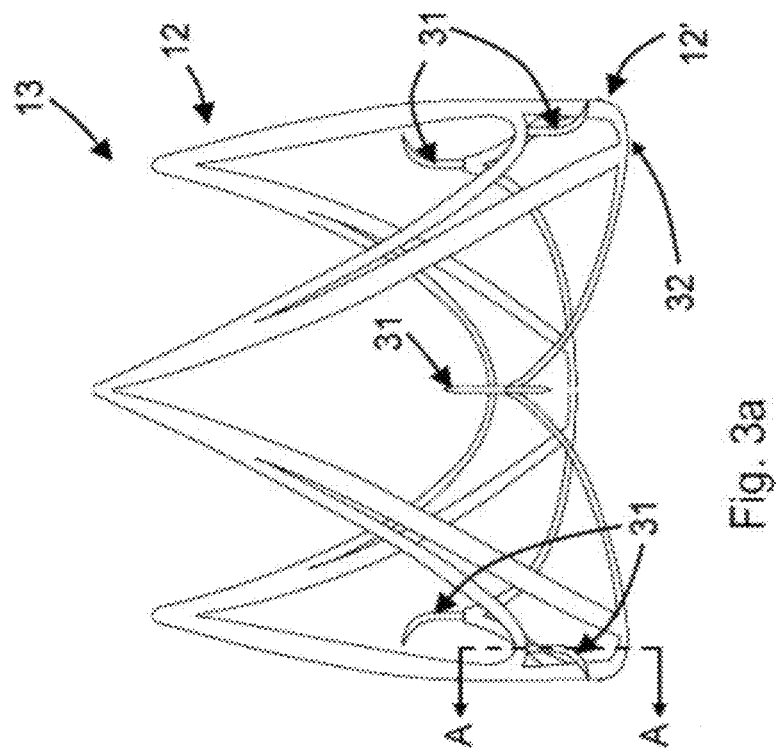
FIG. 3a is a view of a is a valve stent according to the invention in which the crown elements are not parallel to each other.
Figure 2:
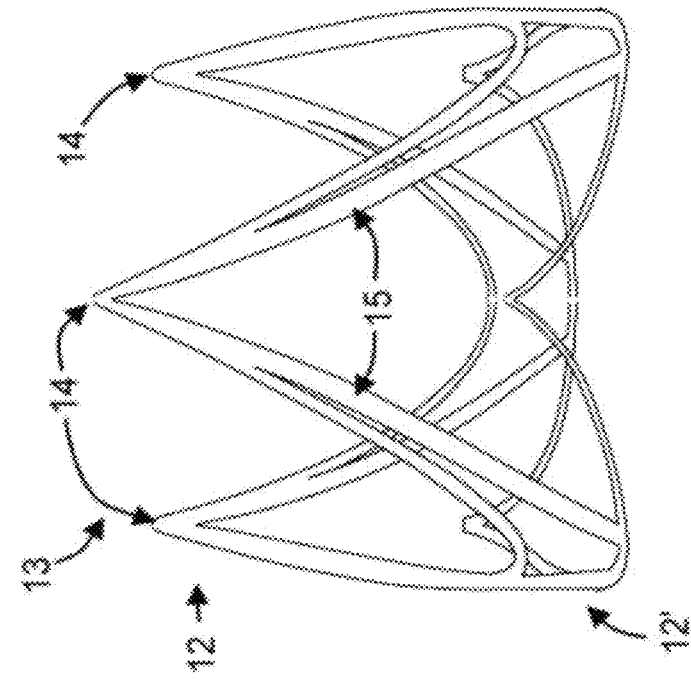
FIG. 2 is a view of a is a valve stent according to the invention in which the crown elements are not parallel to each other.

According to a preferred design of the present invention, as shown in FIG. 1a, for example, it is intended that each of three u-shaped bends 11 are connected to each other at the ends 14 to form a crown element 12. In principle, two or more than three u-shaped bends 11 can be designed. Preferably, two or more crown elements 12 arranged one behind the other form a valve stent 13. Overall, the edge geometry of the leaflets, i.e. the connection line from the valve leaflets to the stent, which is similar to a three-pronged crown, ensures a low and even stress distribution in the leaflets. The clamp forces directed radially inwards are thereby absorbed by the stent, without radial deformation of the ends (commissures) 14 of the valve leaflets towards the inside, which facilitates the opening and closing movement of the leaflets.

Moreover, the preferred stent design features an anatomically adapted design in a natural subanular position. Thus, the aortic bulbs, which are bulbous convexities downstream of the valve leaflets, largely remain free; i.e. as far as possible without hindrance of stent struts or other stent cages, so that the physiological flow conditions in the aortic bulbs are maintained and the openings of the coronary heart vessels (coronary ostia) also remain open to ensure blood circulation through the coronary vessels.

Finally, the valve stent 13 can be folded down to a very small diameter (see FIG. 1b), wherein the leaflets as well as the cylindrically and, if necessary, radially closed wall of the stent can be minimized to a small diameter without permanent deformation or buckling.

A proposed advantage is that the connection bars 15 are wider than the bars of the crown elements 12, wherein the connection bars are preferably twice as wide as the bars of the crown elements 12. With this structure, the valve stent 13 is superlatively stiffened. Depending on its width, the connection bar 15 tangentially clings to the upper course of the crown element 12, so that the bars run nearly parallel to each other or overlap each other over a short distance and contribute to an additional stiffening. Depending on the thickness or width of the connection bar 15, the clamp forces can be absorbed even in case of low buckling of the stent posts or commissures 14; the valve stent structure can, however, be folded extremely gently. This design allows the valve stent 13 to be folded down to a diameter sufficiently small for minimally invasive introduction through femoral arteries or other vessels.

Valve leaflets are preferably arranged at the distal crown elements 12. They are made of a polymeric, biocompatible, elastic and long-lasting plastic. Thereby, the connection line between valve stent 13 and the valve leaflet preferably lies essentially in one plane. The u-shaped crown elements 12 designed in one plane can be folded especially well since the struts can lie very close together in the folded state.

According to another preferred design of the invention, the curves of the crown elements 12 have different shapes, wherein the proximal crown element 12' is preferably flatter than the distal crown element 12. Thereby, the height of the proximal crown element 12' is lower than that of the distal, resulting, especially in the aortic position, in a covering of the cylindric wall in the commissures region of the valve stent with the annulus (native wall of the vessel), which reduces or as far as possible avoids the risk of paravalvular leakage between the aortic bulbs and the proximal region of the crown element 12'. In this design, the proximal crown element 12' does not lie in one plane but is curved towards the commissures 13. The axial distance between the crown elements 12, 12' can be variable depending on the desired covering between valve stent wall and annulus.

The different design of the crown elements 12, 12' has a direct effect on the stiffness of the valve stent 13. If the distal and proximal crown elements have the same height, then the more both crown elements 12, 12' run parallel to each other, the more easily the valve stent 13 can be folded down to smaller diameters. On the other hand, the stiffness to absorb the clamp forces is a bit lower than in the case of a lower height of the proximal crown element 12' towards the distal. Shape designs in which the crown elements 12, 12' are not parallel to each other are shown, for example, in FIGS. 2, 3a, 3b, 4 and 6.

Preferably, the valve stent 13 is self-expanding, wherein the folded valve stent 13 (see FIG. 1b) takes the expanded shape due to its elasticity and/or its shape memory.

Preferably, nitinol is intended as the material. Dimensions of the struts of the valve stent depend on the size of the valve stent used and the purpose—in a vein, an aorta or in a pulmonary position, for example. In a valve prosthesis with a diameter of 10 mm, an exemplary design could include a wall thickness of the struts of at least 0.2 mm, a strut width of at least 0.1 mm and a strut width of the connection bars of at least 0.16 mm. In a valve prosthesis with a diameter of at least 20 mm, an exemplary design could involve a wall thickness of the struts of at least 0.5 mm, a strut width of at least 0.25 mm and a strut width of the connection bars of at least 0.5 mm.

Preferably, the valve stent 13 is formed in one piece, wherein the connection bars 15 can thereby alternatively also be fixed with the crown elements 12, 12' by clamps or other force-locking connections.

Basically, the valve stent 13 can also be used for valves, heart or venous valve prostheses, which are stitched in during a conventional surgical operation (open-heart surgery). For these applications, the dimensions of the struts of the stents can differ from the previously described designs. Because the preferably used memory alloy (nitinol) has higher stiffness, an advantage is that thinner wall thickness can be used for the support housing compared to such support housings made of plastic. Based on the outer diameter, the valve stent thus offers a larger and more effective opening area.

Furthermore, it is intended that the valve stent can also be integrated into a valve-carrying conduit, wherein the advantages of the valve stent, namely its radial flexibility, become particularly clear.

According to another preferred design, it is intended that the valve stent is conically expanded from proximal to distal. Thus, it is adapted to the wall of the annulus in a more form-fitting manner. In addition, the fixing hooks (described below) grip better into the wall of the vessel. Furthermore, in contrast to the preferred use of polymeric valve leaflets, it is also possible to use valve leaflets made of biological tissue as in bioprostheses. A third crown element a short distance to the distal crown element can be used for this purpose. The biological material for fixing with the valve stent can be introduced through the emerging narrow passage. Alternatively, the valve stent can consist of 2-pronged crown elements so that the valve stent is formed as two-leaflet valve prosthesis.

According to a preferred design of the present invention, fixing hooks 31 that grip into the natural vessel wall (see FIG. 3a, 3b) are proposed for secure anchoring of the valve stent in the vessel. As a result it is possible to forego additional fixing elements, lying proximal or distal to the valve stent, which would increase the extraneous surface and thus the risk of developing thrombotic accumulations. Furthermore, additional structures are barriers for blood flow causing blood-damaging turbulences and thus further increasing the previously mentioned risks.

As an advantage, the fixing hooks 31 are arranged to hold the valve stent 13 during stresses and reduce or prevent deformations during the opening and closing processes. Preferably, the fixing hooks 31 are thus arranged at the base 32 of the distal crown element 12 and are (axially) oriented against the flow direction. The tips of the fixing hooks 31 thus point to the proximal direction of the valve stent 12 and are preferably radially curved outwardly so that they grip into the vessel wall. This arrangement is particularly advantageous for the closing process of the valve, since closing pressure and fixing hooks 31 are oriented in the same direction, because the highest pressures occur in the closed state, wherein the base 31 of the stent bends is presses radially outward, whereas the commissures 14 are curve radially curve inward. The fixing hooks can thus grip quite well into the vessel wall, since they grip into the vessel wall in a kind of wedge effect by the radially outwards directed forces of the arch-shaped stent base 32. The fixing hooks 31 can be arranged not only at the bases 32 of the distal but also at the bases 32 of the proximal crown elements 12, 12', wherein in latter crown element 12', they can still be oriented in flow direction. More than one—two or three fixing hooks 31 side by side, for example—can optionally be arranged in the positions described for fixing hooks 31 (see FIG. 3b).

Another preferable position of the fixing hooks 31 are the ends 14 of the proximal crown elements 12'. In this case the fixing hooks 31 are, however, oriented the other way round in flow direction and also curved radially outward. Therefore, the fixing hooks 31 are oriented in direction of the flow forces acting on the valve stent, since the commissures 14 are pressed radially outward by the opening pressure during the opening process and thus the fixing hooks 31 are driven into the vessel wall. This arrangement of the fixing hooks 31 at the commissures 14 of the valve stent 13 is particularly advantageous if the valve stent 13 is widened from proximal to distal and clings to the native annulus. The wedge effect described above acts here in the opposite direction.

The arrangement of fixing hooks 31 in flow direction can in principle also be carried out at the ends of the distal crown elements 12, wherein, however, it is advantageous to position the fixing hooks further downstream using struts.

The fixing hooks 31 can also be oriented in circumferential direction. Moreover, the arrangement of the fixing hooks 31 at the base 32 of the bends and/or ends 14 of the crown elements 12, 12' can also be applied for other geometries of valve stents.

Preferably, the fixing hooks 31 are made of the same material as the valve stent 13. A super-elastic alloy or a shape memory material such as nitinol is suitable for this purpose, so that the complete valve stent 13 can be produced in one piece. The curved shape of the fixing hooks 31 intended for the final state, the implantation state, must be produced using an appropriate transforming and heat-treating process. For the implantation procedure, however, the fixing hooks are bent once more into a straight shape, so that, following folding, the valve stent 13 can be introduced into the lock of the catheter. The straightened shape of the fixing hooks 31 can be used to fix the valve stent 13 with additional devices, over soluble clamps in connection with positioning wires, for example, and to bring it out from the catheter and to position it at the implantation site. After releasing it from the lock, the valve stent 13 unfolds itself to its final diameter and the fixing hooks 31 extend radially outward to their fixing position.

Altogether, the valve stent 13 with the fixing hooks 31 features excellent maneuverability, wherein the particularly short design allows the valve stent 13 in the folded state to be very easily maneuvered through curved vessels such as the aortic arch, for example.

According to another design, it is intended that the fixing hooks 31 are made of a shape memory alloy, in particular nitinol, with a shape transformation temperature above body temperature and that they are fixed to the valve stent by welding, for example. Thereby, the fixing hooks 31 already have their curved shape. For loading, i.e. introduction into the lock, they are also straightened so that they are axially oriented as far as possible and, if necessary, are also connected to the positioning wires. Then the valve stent is folded and introduced into the lock. After pushing it out from the lock, the valve stent unfolds itself and is exactly positioned at the implantation site, wherein the fixing hooks initially maintain their straight, axial alignment. Only after reaching the final position are the fixing hooks warmed up to their shape transformation temperature (e.g. using electric current or an alternating magnetic field) which lies above body temperature and triggers the shape transformation function of the fixing hooks 31 and transfers them to their extended position. The fixing hooks 31 grip into the vessel of the patient and the valve stent is thus finally anchored in the vessel.

If fixing hooks 31 are made of a memory alloy with a transformation temperature below body temperature or simply of a super-elastic alloy, there is the possibility of temporarily preventing the extension of the fixing hooks 31 by mechanical limitation such as soluble clamps, for example, as will be explained later.

The fixing hooks 31 and the valve stent 13 can alternatively also be made of different alloys. The valve stent, for example, can be made of a non-self-expanding material to which the fixing hooks, made of shape memory material or the super-elastic alloy, are connected. Preferably, in this case the transition region between valve stent 13 and fixing hooks 31 is at least made out of one piece, so that the weld as a potential imperfection site is not within the stress zone.

Furthermore, the valve stent can also be made of a shape memory alloy whose shape transformation temperature is above body temperature.

Finally, as an advantage, radiographic markers are arranged at the valve stent so that better radiographic presentability is guaranteed.

The wall of the valve stent is preferably made of a very smooth, particularly porous membrane consisting of biocompatible plastic. Due to this porous structure, there are other fixing possibilities for the valve stent in the vessel, which can be combined with the fixing hooks, such as gluing, minimally invasive suturing with threads or self-closing clips ("endo-clips").

Another issue is the treatment of congenital heart valve defects in newborns and children requiring, among other things, a reconstruction of the right ventricular outflow tract (RVOT). For this purpose, so-called valve-carrying conduits (conduit valves) are used; these are heart valves integrated into vessel prostheses. According to the prior art, there are no known heart valve substitutes with growth potential, so that a repeated operative revision of the RVOT is required for these patients to adjust the size of the heart valve prosthesis to the growth of the patient.

Thus, according to another design of the present invention, flexible wires 41 are intended (see FIG. 4), the free ends of which are fixed to two adjacent connection bars 15. Preferably, the flexible wires 41 are fixed with clamps 42 to the connection struts 15, wherein the clamps 42 and/or the wires 41 are made of shape memory metal. Thus, the valve stent 13 can temporarily be held in an intermediate position between a completely folded state and a completely unfolded state. The valve stents 13 with solid and dotted lines show this schematically in FIG. 4. It is possible to inhibit the unfolding of the valve stent to the larger diameter through the length of its wires 41. In relation to the diameter of the valve stent in its final shape, the diameter can be locked between 70% and 100% of the final diameter.

The self-opening clamps that hold the wires are preferably made of a shape memory alloy, especially nitinol with a shape transformation temperature above body temperature. A valve stent designed in such a way is implanted in children in a minimally invasive procedure. Only once the valve becomes too small compared to the rest of the growing organism does a temperature impulse, generated by an electric current or an alternating magnetic field, for example, increase the temperature of the clamps or wires above their critical shape transformation temperature so that they open and the valve prosthesis can gradually unfold itself to its final diameter. The energy for further unfolding of the valve stent due to its self-expanding properties is sufficient enough to deform the tissue structures that have become ingrown in the meantime. The valve stent must thus have struts or connection struts of appropriate width and thickness.

The conditionally switchable inhibition of unfolding can also be relieved by other constructive details such as the wires, which are fed through the connection struts of the valve stent. For this purpose, wires or other thin struts can be attached over the struts using clamps.

This constructive design allows the possibility for the heart valve prosthesis to remain in vivo in the child over a longer period. Thus, a re-operation usually required several times can be avoided until adulthood.

The use of the gradually expandable valve stent can also be advantageous, if the valve stent is implanted in a vein as a venous valve and the vein dilates, whereby the radial pressure from the valve stent to the vessel significantly decreases and the valve stent can lose its secure anchoring.

In addition to the valve stent described above, it is advantageous to widen the annulus or the vessel using further anchoring elements, since the valve stent alone does not have enough tensioning capacity to widen the annulus. These anchoring elements can also press the native leaflets or a different constriction of the annulus radially outwards and thereby, if necessary, increase the diameter of the annulus or the vessel. Alternatively, artificially formed bulbs can be formed by these anchoring elements. Furthermore, the correct size selection can be improved with these additional elements, so that the valve stent unfold itself to its optimal diameter and correct functioning of the valve prosthesis is ensured.

According to the prior art, different possibilities are known for fixing a percutaneous aortic valve in the annulus or bulbs. For example, it is described that the percutaneous prosthesis is held in a form-fitting (cf. DE 101 21 210 B4) or force-locking manner (cf. US 2006/0265056 A1) in the aortic annulus, wherefore stent structures are used that radially widen themselves and thus cling to the bulbs. One disadvantage is that these stents have many meshes or stent struts, which at worst can lock the coronary ostia. Another is that an extensive, extraneous structure is hereby created, which is associated with known problems.

According to a preferred design of the present invention, a separate anchoring stent 51 is thus intended (see FIG. 5), having at least one or more than one crown element 12, 12', wherein the separate anchoring stent 51 can be placed between the crown elements 12, 12' of the valve stent 13, so that the separate anchoring stent is positioned within the valve stent 13. Analogous to the valve stent, the connection of the crown elements 12, 12' to the anchoring stent 51 is preferably carried out using connection bars 15. Alternatively, other bars that are axially or completely differently shaped, for example undulated meshes, can be intended. Preferably, the distance between the crown elements 12, 12' is smaller than the distance from the crown elements 12, 12' of the valve stent 13, so that the anchoring stent 51 fits between the crown elements 12, 12' of the valve stent and is thus positioned within the valve stent. The anchoring stent 51 can also deviate from a circular cylindrical shape. Thereby, the anchoring stent can have protrusions and indents in a circumferential direction to the surrounding of the connection bars 15 or other bars, so that the valve stent 13 and the anchoring stent 51 are connected with a bayonet-type lock, wherein this lock preferably opens not by turning but by radial expansion of the valve stent 13 in the anchoring stent 51.

The anchoring stent, especially the bayonet-type lock, can be designed in such a way that the distal crown element of the anchoring stent is positioned within the two crown elements of the anchoring stent and that the proximal crown is proximally positioned to the crown element 12' of the valve stent. The distance between the crown elements in the base region of the valve stent can then be even larger than that of the valve stent.

In order that the anchoring stent can also be used for application with a percutaneous venous valve prosthesis, according to a preferred design, a bulb stent 61 is intended, which forms artificial bulbs by widening vessels in a bulb-shaped manner, (see FIG. 6, 7a-7f, representing only ⅓ of the bulb stent). Thus, the bulb stent 61 is fixed in the vein in a form-fitting and force-locking manner. The bulb stent 61 has as few meshes or bars as possible, which minimizes the extraneous surface so that very few hindrances for blood flow are formed. Preferably, as shown in the radial top views in FIG. 7a-7f, two cross-shaped stent struts 63, 63' are basically arranged to form a bulb 62. In a radial and circular direction, the stent struts are designed in such a way that the artificially formed bulbs 62 are similar to the sinuses of natural aortic valves so that a favorable blood flow is made possible with circular flow behind the leaflets, with a gradual and gentle valve closure. The cross-shaped stent struts 63, 63' are oriented in the flow direction (and top view) in an x-shape, wherein three of such x-shapes are connected to each other at their ends in a cylindrical arrangement to form the bulb stent 61. This results in a xxx-base shape in a plane projection. The crossing points 64 of the x preferably form the points with maximum radial extension into the bulbs (see FIG. 6).

Figure 7A:
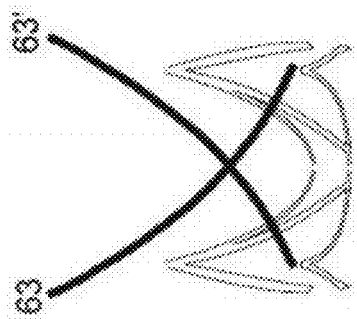
FIG. 7a is radial top view showing two cross-shaped stent struts arranged to form a bulb stent.
Figure 7B:
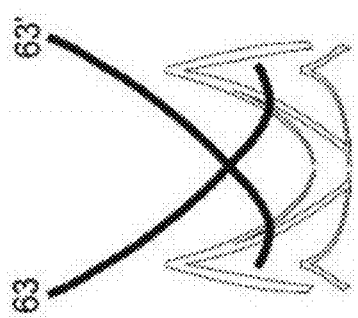
FIG. 7b is radial top view showing two cross-shaped stent struts arranged to form a bulb stent.
Figure 7C:
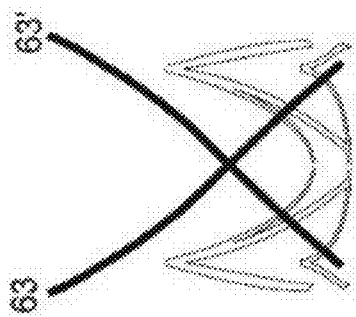
FIG. 7c is radial top view showing two cross-shaped stent struts arranged to form a bulb stent.
Figure 7D:
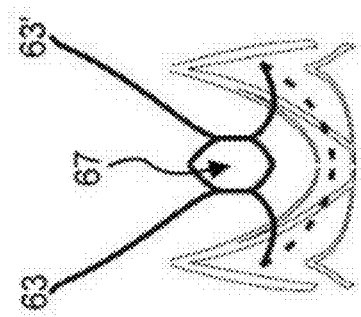
FIG. 7d is radial top view showing stent struts arranged to form a bulb stent.

Different designs are possible for the bulb stent with its three x-shaped crosses (FIGS. 7a-7f). Thus, the xx connections can be connected with each other not only at an angle but also in an arch-shaped manner. The proximal, upstream-side xx connections are preferably designed in such a way that they are positioned in a circumferential direction between the proximal and the distal crown elements of the valve stent in the region of the commissures (in FIG. 7 positioned outside) and their tips point not in the proximal direction (FIG. 7a) but the ends are directed in an arch shape towards each other and their tips point in the distal direction (FIG. 7b). A further stiffening option of a bulb stent 61 is an additional bend in the shape of a strut, which is positioned below the x and is docked with its ends to the proximal xx connections (FIG. 7d).

Figure 7E:
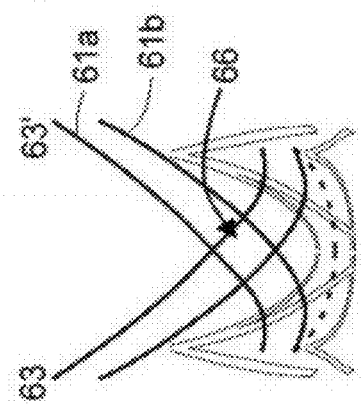
FIG. 7e is radial top view showing stent struts arranged to form a bulb stent.
Figure 7F:
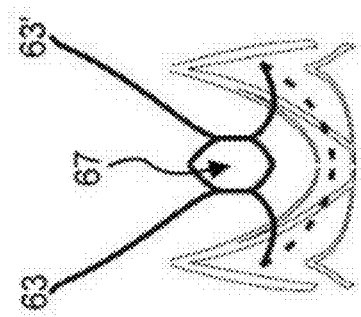
FIG. 7f is radial top view showing shaped stent struts arranged to form a bulb stent.

According to another design, it is intended that two bulb stents are axially offset to each other 61a, 61b, so that they form a central diamond-shaped opening 66 in the region of the crossing points (FIG. 7e). This specific design is particularly suitable for creating additional stiffening or for distributing or even increasing the power to shape the bulbs in the vein. If the bulb stent 61 is used in the aortic position, the diamond-shaped structure will be so arranged that the openings 66 for the coronary arteries are positioned in their middle. Another possibility to avoid obstructing the ostia is to design the bulb stent so that it is dissociated at the crossing point and a diamond-shaped or even circular to rectangular opening 67 is generated in between by correspondingly shaped struts (FIG. 7f). The openings 66, 67 generated by the struts in the bulb cage can also be arranged asymmetrically within an individual bulb.

Figure 8:
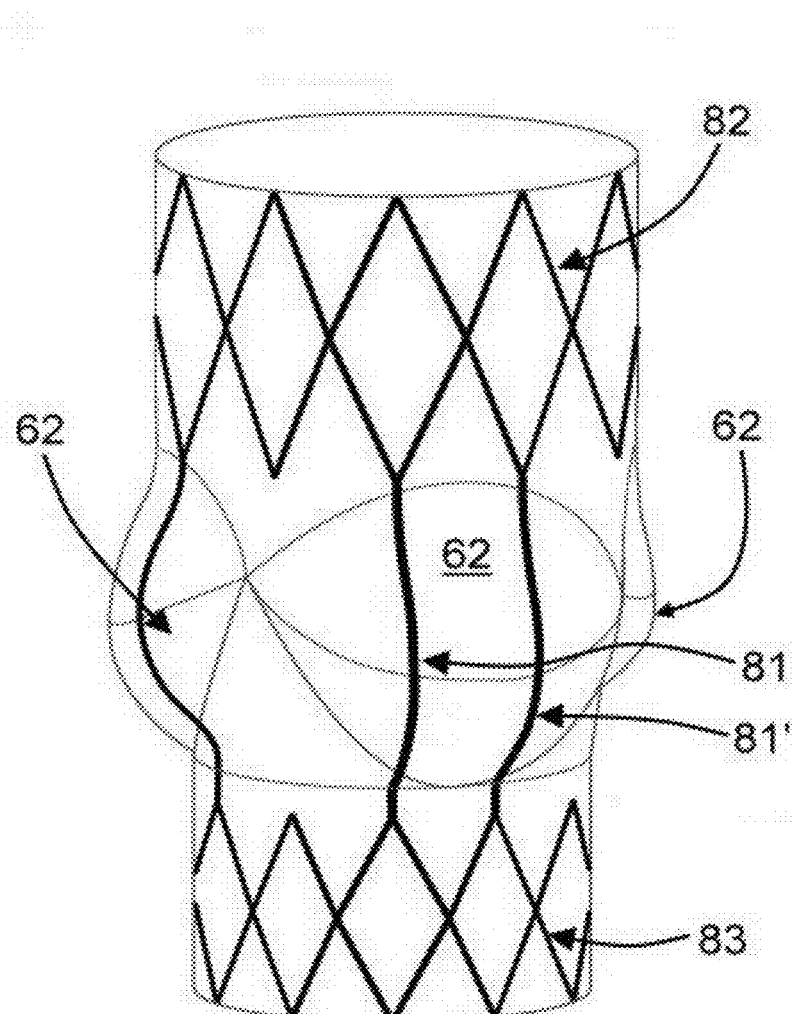
FIG. 8 is a view showing struts running in an axial direction that form the bulbs.

In another, further design, struts 81, 81' running in an axial direction preferably form the bulbs 62, wherein two struts are preferably intended for each bulb (see FIG. 8). The struts 81, 81' are arranged at such a distance that the ostia are between them.

The struts 81, 81' of the valve stent that form the bulbs are preferably arranged in a cylindrical shape in cross-section. The axially directed struts 81, 81' are connected to conventional mesh-like stents 82, 83 at their ends (FIG. 8) or distally, to a stent that is similar to the anchoring stent 51 or proximally to the anchoring stent itself or to the valve stent 13.

The bulb stents preferably have a diameter up to approximately 30% larger at their flow outlet, i.e. at their distal end, than at their inlet, which is equivalent to the geometry of the natural annulus in the aortic position. Thus, the bulb stent 61 can be better anchored in the vessel in a form-fitting or force-locking manner.

The bulb stent 61, as well as the anchoring stent 51, can preferably be formed in one piece. If the bulb stent 61 is cut from a straight, cylindrical tube, the bulbs 62 must subsequently be shaped using appropriate transforming and heat-treating processes. Alternatively, the bulb stent 61 is made of three previously individually produced x structures which are bonded by welding, for example.

In principle, the same materials can be used for the bulb stent 61 as for the valve stent 13 or the anchoring stent 51. Moreover, the bulb stent can also be equipped with radiographic markers, as can the valve stent 13 or the anchoring stent 51.

Furthermore, fixing hooks 31 are intended for additional fixing, not only for the anchoring stent 51 but also for the bulb stent 61. Here, as for the valve stent 13, fixing hooks 31 made of a nitinol alloy with a transformation temperature above body temperature is recommended to extend the fixing hooks 31 only right at the end following application, unfolding and final positioning of the valve prosthesis. The fixing hooks 31 can furthermore be used as holding points for the clamps of the positioning wires of the catheter to extend and position the stents.

The connection between bulb stent and valve stent can be made in various ways. Preferably, the bulb stent and the connection struts of the valve stent are connected by threads. Hereby, depending on tightening of the threads, a flexible connection is generated between the two stents, so that both stents can be moved against each other, which is advantageous for the folding process for introducing the stents into the catheter. The stents, preferably made of nitinol, can alternatively be welded or glued at certain points. The latter is particularly advantageous if at least one of the two stents has a sheathing or surface layer made of a polymeric, preferably porous membrane in the overlap region of the two stents, preferably in the base ring area of the valve stent.

As another alternative, the fixing hooks of the valve stent can grab into the anchoring stent. That leads to a fixing of the valve stent with the anchoring stent. Alternatively, with the design described above with the bayonet-type lock in the region between the distal and proximal crown element of the valve stent, a connection can be formed between both stents. The latter two connection possibilities imply that the two stents are applied in two steps; that is, the bulb or anchoring stent is introduced and positioned first, followed by the valve stent. Hereby, it will make sense to ultimately use the previously described temperature impulse to increase the temperature of the fixing hooks above body temperature for extension of the hooks and thus for the final fixing of the valve prosthesis, even if the hooks are only connected to the bulb or anchoring stent. This allows for additional final, finer adjustments of valve and anchoring stents already joined together at the intended implantation site.

Alternatively, the bulb stent can additionally be sewed on in the vessel in a minimally invasive process. For this purpose it makes sense to use self-closing clips made of a memory alloy ("endo clips") or simple threads, for example.

Due to the form-fitting and/or force-locking anchoring function of the bulb stent, the previously described fixing possibilities such as gluing or sewing on of the bulb stent are not necessary but represent support measures depending on the version and design of the bulb stent, for example the tensioning capacity among others.

The bulb stent should preferably be used in the venous valve prosthesis but can also be applied in aortic, pulmonary and tricuspidal positions like the anchoring stent. In addition, the anchoring stent and the bulb stent can function in pressing the remaining native leaflets radially outwards. If the bulb stent is used orthotopically in combination with a venous valve prosthesis, the bulb cage can also press the native leaflets radially aside. Since natural venous valves almost exclusively form valves with two leaflets, the bulb stent generates an annulus with three bulbs from a two-leaflet natural annulus. In an alternative design, the bulb stent can also be applied as stent with two bulbs in combination with a two-leaflet venous valve prosthesis.

As described previously, the bulb stent in appropriate design has enough tensioning capacity to widen the annulus with the native valve leaflets possibly not removed beforehand. However, the bulb stent is again somewhat pressed by the counter-force of the annulus, which could inhibit the complete unfolding of the valve prosthesis. As a result, the functionality of the valve prosthesis can be restricted in the operative state. An elastic buffer or a radial clearance is generated by the bulb stent and the covering of the valve stent and, if necessary, the bulb or anchoring stents, to balance their unpredictable reset and to let the valve stent unfold to its complete diameter.

Finally, the valve stent can be connected directly on or at a distance from its distal and/or proximal end using connection struts to mesh stents that are commonly known in the prior art, without a shaping of bulbs.

The easy and exact positioning of percutaneous valve systems is an important property of catheter systems, especially since the visualization possibilities of modern imaging procedures are continually improved. The exact positioning of stents is, however, subjected to narrow limits so far, since existing application devices work exactly only to a limited extent.

It is therefore the task of the present invention to create a device for application of a stent that facilitates the exact positioning of the stent.

This task is solved by the device which includes positioning wires with clamps at their ends, which can be connected to the fixing hooks at the ends of the crown elements in a force-locking manner. The self-opening clamps 91 are laid around the precisely bent claws or fixing hooks 31 and are fixed in a force-locking manner using specific crimping pliers (see FIG. 9a, 9b). Especially in FIG. 9b, a fixing hook 31 with attached clamp 91 is shown from the perspective of cutting line AA (compare FIG. 3a). Thus, the fixing hooks 31 are fixed in this straight shape, even if the temperature of the fixing hooks 31 is above the transformation temperature and, hence, the fixing hooks 31 return to their curved shape, caused by their shape memory or simply due to their intrinsic elasticity. By means of the positioning wires 92, the valve stent 13 is connected to the catheter system and can be positioned after pushing the valve stent out of the lock that is axially movable in or against flow direction and also rotatable in a circumferential direction. This procedure is not only limited to the application of valve stents, but can also be used for vessel stents and/or stent grafts (covered stents) possessing suitable fixing hooks.

If the valve stent is introduced into the body in the flow direction of the blood (anterograde), hence over the heart apex to the aortic valve, for example, then the clamps 91 will be preferably connected to the fixing hooks 31, which are positioned at the bases 32 of the crown element 12. This positioning of the clamps 91 to the fixing hooks 31 also facilitates the repositioning of the valve stent 13 into the lock, since this position is nearest to the lock and a tapered shape favourable for repositioning is generated. As the positioning wires are pulled into the catheter, a radial tension on the bases of the stent arises that guides or pulls the stent again into its folded position.

If the valve stent 13 is introduced into the body against the flow direction of the blood (retrograde), for example transfemorally up to the aortic valve, then the clamps 91 are preferably connected to the fixing hooks 31, which are positioned at the ends 14 of the crown elements 12, 12', preferably at the ends of the proximal crown element 12 of the valve stent 13. This positioning of the clamps 91 facilitates the repositioning of the valve stent 13 in the lock, since pulling back generates a favorable, tapered shape by the radial tension of the positioning wires 91.

Figure 9:
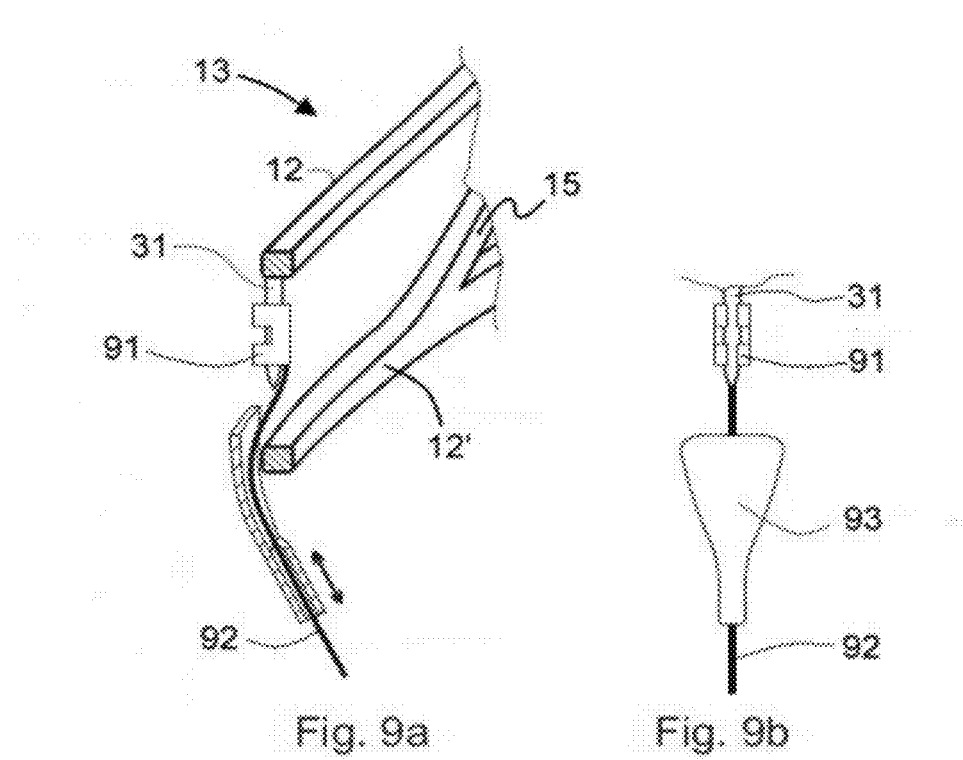

The positioning wires 91 can furthermore have radially (outward) oriented coverings 93, in which the positioning wires can be introduced and moved. This further facilitates the repositioning into the lock and interlocking or wedging of the tips of the distal valve stent crown with the lock will be avoided if the clamps are applied in a retrograde manner. In this case, the coverings 93 preferably overlap the ends 14 of the distal crown of the valve stent. The proximal region of the covering is extended proximally toward the outside of the catheter in the shape of a flexible tube, so the coverings can also be moved axially at the positioning wire 92 to bring them in position only when needed. Thereby, the covering 93 can also be made as a single piece together with the positioning wires 92, so that the coverings are integrated into the positioning wires 92. Furthermore, the coverings can overlap the clamps if necessary. FIG. 9 shows an arrangement of clamp and covering for an anterograde application.

For anterograde as well as for retrograde application of the valve stent 13, it is preferably intended that three positioning wires 92 lead the valve stent and the valve and position the valve stent 13. However, more than three positioning wires 92 can also be used. Preferably, fixing hooks 31 made of a shape memory alloy are used, the transformation temperature of which is above body temperature, so that the extension of the hooks is switchable by means of a temperature increase following the final positioning of the valve prosthesis. If more fixing hooks 31 than positioning wires 92 are intended at the valve stent 13, then at least the surplus fixing hooks 31 must be made of such an alloy or the extension of the fixing hooks 31 must be hindered using mechanical stops or fixations, so that the valve stent can still be positioned. Therefore, it is intended that the surplus fixing hooks 31 are fixed by clamps which are not connected to a positioning wire 92, wherein the clamps can be specifically opened by an increase in temperature. Hereafter, the clamps preferably remain in the surface layer of the valve stent 13. Hereby is above all the advantage that none of the hooks 31 must be made of a different or additional alloy. The clamps will also remain in the surface layers if the clamps function to fix not only the fixing hooks but also the positioning wires at the same time; that is, the positioning wires are not made as one piece with the clamps.

According to another preferred design, it is intended that the positioning wires 92 are glued to the fixing hooks or to another region of the stent 13. Hereby, (conditionally) soluble biocompatible glues are used, for example. This could be a glue to which a powder made of superparamagnetic particles is added, for instance. These consist of iron oxide, which is embedded in silicon dioxide nanoparticles. The glues are then exposed to a high-frequency magnetic field. For this procedure to work, at least one of the components to connect must be electrically non-conductive.

Figure 10:
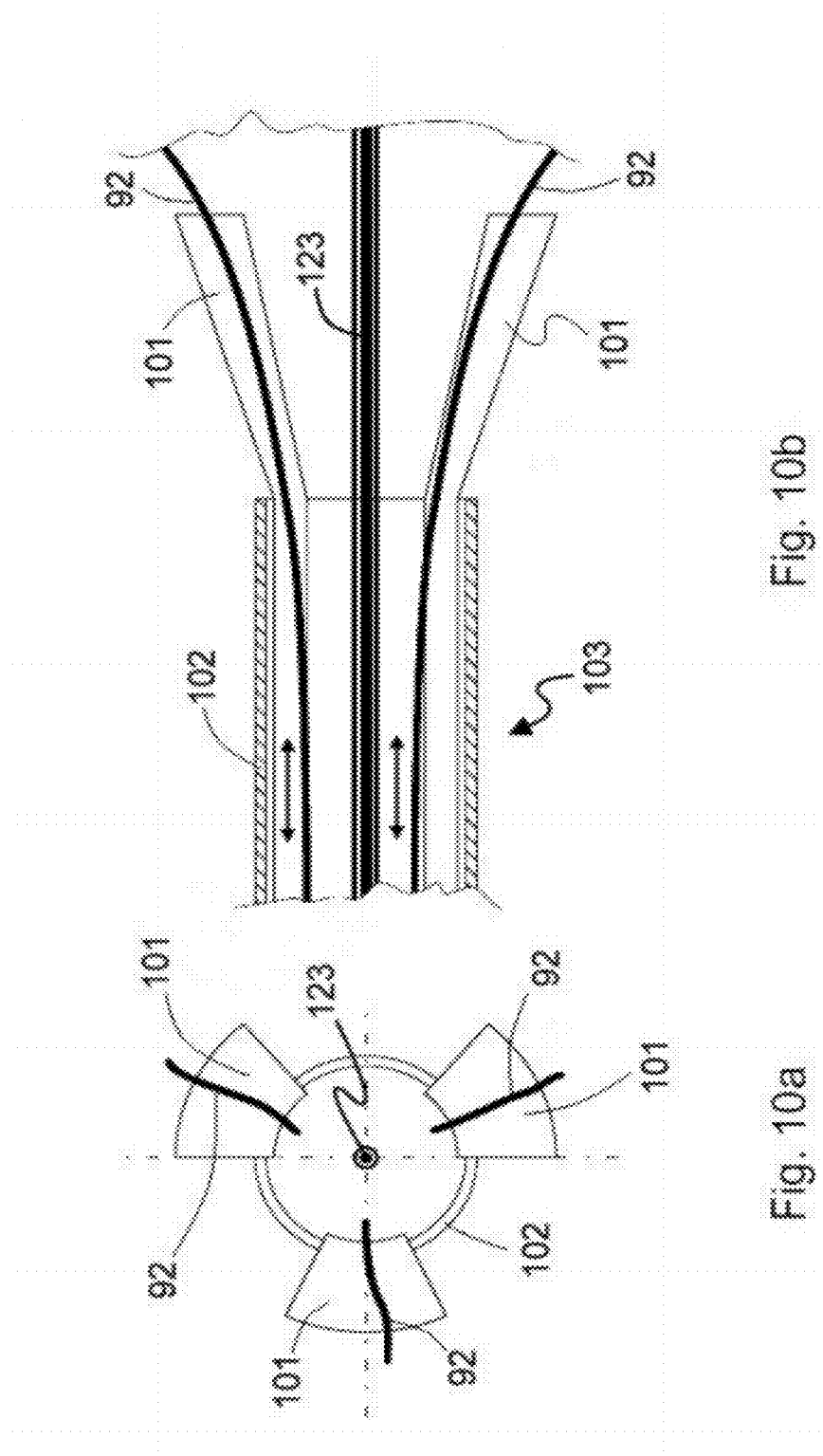
FIG. 10a is an end view of a lock provided with three funnel-shaped elements extendable from the lock.
FIG. 10b is a side sectional view of a lock provided with three funnel-shaped elements extendable from the lock.

Using clamps 91 and positioning wires 92, the stent can also be pulled back into the lock. The positioning wires 92 are positioned in such a way that, during their repositioning, the bases 32 (in case of anterograde application) or the ends 14 (retrograde) are radially pulled inward and so inserted into the lock. Basically, this method can already be used for the loading before application immediately prior to operation. For repositioning capability as well as for loading, the lock can be provided with three funnel-shaped elements extendable from the lock (withdrawal aid) 101, which simplify repositioning of the valve prosthesis into the lock 102 (FIG. 10) or loading.

To achieve the positioning capability of the valve, however, mandrels and pins without arch-shaped hooks are also sufficient, which then only function as hold or guidance points for the clamps of the positioning wires.

The principle of the fixing hooks or mandrels can also be used for bulb stents and anchoring stents. In addition, the clamps of the bulb stents can also be fixed at one of its struts. The connection of the fixing hooks to the stent struts can also be applied for valve and anchoring stents as well as for vessel stents and/or stent grafts (covered stents).

The positioning wires are preferably designed as compression springs so that the valve can be pushed out more easily using clamps and positioning wires. Alternatively, the extension of the valve can also be carried out by pulling back the catheter or the lock.

Figure 11:
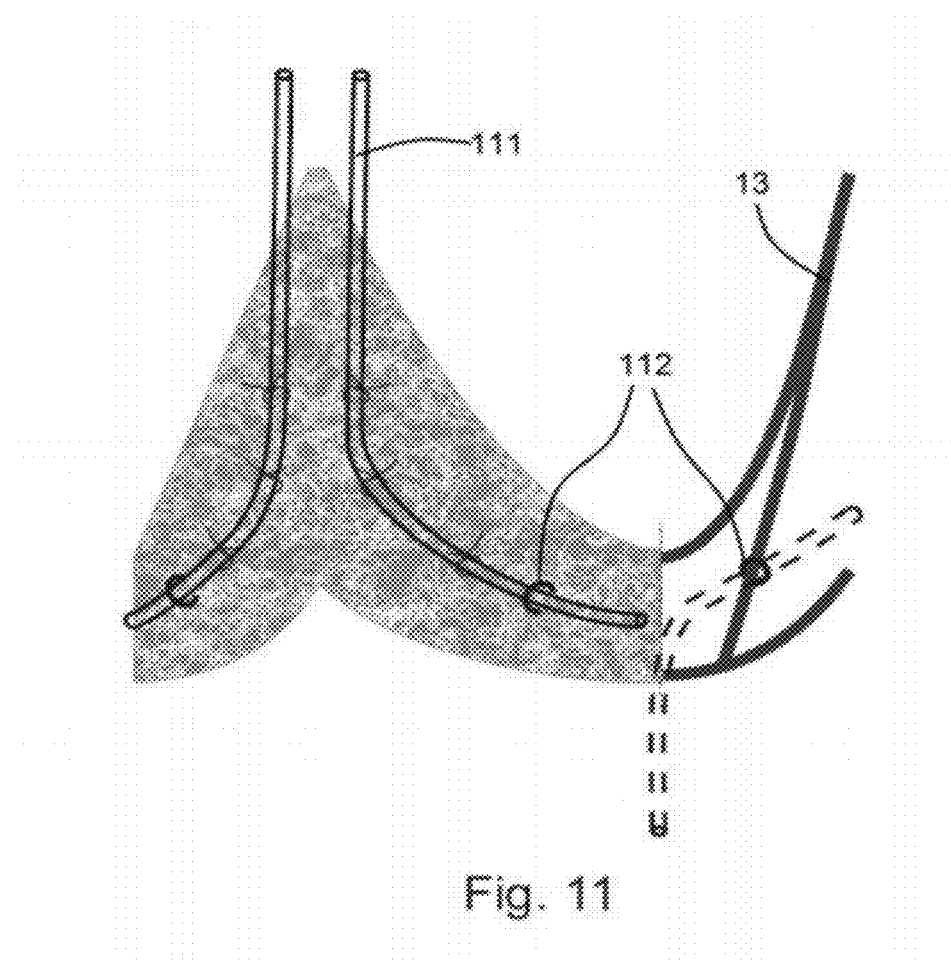
FIG. 11 is a view showing additional flexible tubes used as a guide to position the valve stent with the left half showing a retrograde and the right half showing an anterograde (as dotted line) application.

FIG. 11 shows an image in the left half of which shows a retrograde and the right half an anterograde (as dotted line) application. On the left side, a surface layer such as a fleece, for example, is indicated.

An alternative design for positioning and fixing the valve stent 13 within the vessel or annulus is carried out via additional flexible tubes 111, which on the one hand supply glue to adhere the prosthesis to the annulus and on the other hand can be used as a guide to position the valve stent (see FIG. 11). The flexible tubes 111 are here preferably connected to the valve stent using the connection bars 15 of both crown elements 12, 12' by a self-opening clip 112 or a self-opening clamp. At the same time, the clip can thereby be used as a lock for the supply to regulate the glue exportation. This will be especially advantageous if a clip with a shape memory alloy with a transformation temperature above body temperature is chosen, so that the clips are opened only after the final positioning of the valve stent. However, different locks can also be used or a lock can be avoided completely if the valve is guided and held by the positioning wires. The flexible tubes or glue pipes are guided along the arch-shaped base rings through the loops. The loops in turn go through the porous wall. Depending on the diameter of the glue pipe, the pipe can also be guided directly through the porous wall in some places. Following final positioning, the glue supply is triggered by opening of the clips, if necessary, and thereby the glue pipe is withdrawn and the glue is continues to be released. The design will be advantageous for the repositioning and the glue supply via the complete base ring if six pipes are used for a three-leaflet valve stent (for a two-leaflet valve, four pipes respectively).

The flexible tubes 111 (glue pipes) can also have "coverings" 93. If the glue pipes are connected to the valve stent by clips, clamps or other elements, appropriately designed glue pipes, as well as the positioning wires, can be used to position the valve prosthesis and also to reposition the valve prosthesis into the lock. Likewise, the glue pipes can be used just as the positioning wires for loading of the valve prosthesis, as described below for positioning wires.

The bonding can be carried out without or in combination with the fixing hooks. The design with fixing hooks is advantageous since the valve stent is already held in the annulus, so there is no risk of migration of the valve prosthesis when the glue pipes are pulled back and from the tractive forces arising thereby.

Preferably, a funnel-shaped device 121 is arranged around the lock 102, by which the valve stent 13 can be introduced into the lock 102 of the catheter 103. In other words, an additional funnel-shaped device 121, attachable around the lock 102, can be used to load the valve stent 13 as well as the anchoring stent 51 or the bulb stent 61 in the operating room before application, to enable the introduction of very sensitive valve stents 13 as well as anchoring stents 51 or bulb stents 61 into the lock 102 of the catheter 103 without damage (see FIG. 12a, 12b). The funnel-shaped device 121 is arranged between the lock 102 and the valve stent 13, through which the positioning wires 92 with the clamps 91 are guided to fix the prosthesis. The device can be formed in separate pieces.

The valve stent is preferably delivered in a preassembled state; that is, the clamps 91 of the positioning wires 92 are already connected to the valve stent 13, which is located in the funnel-shaped device 121 (FIG. 12a). To load the valve, the positioning wires must simply be pulled back until the valve stent 13 or the other stents 51, 61 or the valve stent 13 in combination with the other stents are located within the lock 102 of the catheter 103. Subsequently the lock head 122 is closed (see FIG. 12b).

Depending on whether the intended application is antero-grade or retrograde, the valve prosthesis must be mounted in the opposite direction into the lock 102. FIGS. 12a and 12b more importantly show the guide wire 123, which is, however, not required for loading.

In addition, the glue pipes can be attached and fixed to the valve stent, into which they are guided through the catheter and the applicator like the positioning wires. If necessary, the glue pipes are used for the loading, if positioning wires are renounced.

Alternatively, an elastic flexible tube, in which the valve is arranged and the diameter of which is dependent on an axial directed force, can be intended for compression of the valve stent. The valve stent is folded by the radial taper of the flexible tube. To compress the valve stent to a defined diameter so that it can be introduced into the lock, it is recommended to pull the stretched tube subsequently trough a funnel which can be arranged around the tube. If the procedure is carried out at a temperature below the shape transformation temperature of the valve stent, then the valve stent, following relief of the tube, can be taken from the tube in folded state and inserted into the lock of the catheter. The advantage of the previously described loading device is that the removal of the valve stent from the tube and subsequent insertion into the lock can be omitted and is carried out by only one procedure, the withdrawal of the positioning wires.

The structural design and the procedure to produce the valve stents are of great importance for the functionality of the valve stent, including sufficient opening and closing without (paravalvular) leakage and the highest possible fatigue strength of the percutaneous implantable valve stent.

The materials preferably used for the valve stent are memory metals, particularly nitinol, and for the attached structural valve design are biocompatible, elastic, long-lasting polymers, especially polyurethanes. However, other materials can also be used such as silicones, PTFE, poly-sulfones, various models of the polyurethane group, polyvinyl alcohol, polystyrene/block/isobutylene/block/styrenes, hydrogenated styrene/block/copolymers or other polymers known from the prior art, which are suitable for cyclic loads. In addition, other shape memory alloys can be used.

The cyclic pressure load of the blood is transmitted via the valve leaflets to the valve stent, i.e. the struts of the stent. Since the areas of contact between the leaflets and the thin stent struts are very small, the bonding and/or the adhesion between nitinol stent and polymeric valve stent must be sufficiently well designed.

One initial possibility is to produce sufficient adhesion of the polymer to the stent cage and to improve the existing adhesion procedure. To improve adhesion, the surface can be treated by mechanical or chemical roughening, plasma cleaning or plasma coating or coating with other thin layers, primers such as reagents for silanisation or possibly also glues, for example, wherein, however, all such procedures or materials must be chosen such that they are very biocompatible. Alternatively, the treatments listed to improve adhesion of the surface can be combined with subsequent application of a biocompatible glue. Since the polymers used normally have fewer free end groups that can combine with the primers, the adhesion results are not optimal.

According to a preferred design, it is thereby intended that the valve stent is coated with a coating material that preferably exhibits hardening increasing from the inside to the outside or decreasing hardenings or hardenings at first increasing and then decreasing.

According to a specific design, it is furthermore intended that the coating material is a hyperbranched polymer (e.g. polyethyleneimine) or a base polymer (SPUR) for silanised polymers. Both result in much better adhesion to the substrate of the stent material. Hyperbranched polymers are highly branched and highly functional at the molecule surface and therefore offer a huge number of binding sites to stick to surfaces or primers compared to reagents for silanisation. Alternatively, it is here intended to modify with hyper-branched properties the polymer of which the valve stent or the leaflet material is made (preferably polyurethane) for the first contact layer to the stent. The chemical structure of polyurethane could here be modified in such a way that it is hyperbranched. Hyperbranched polyurethanes are very efficient molecular anchors and increase the number of adhesion groups at the surface.

Another process that can if necessary be combined with the previously described procedure to improve force transmission, involves the composite structure of the plastic for the stent frame. The stiffness or elasticity of the stent is normally much higher than that of the plastic of which the leaflets are made. In one approach, the stent or the stent struts can successively be coated with plastics with a decreasing degree of hardness. For this purpose, very hard PU can initially be used followed by a medium and/or soft PU to achieve a gradual transition with more favorable force transmission from the hard stent to the soft leaflet. Thereby, the struts are preferably completely enclosed by each layer. To distribute the force transmission over a larger adhesion area at the struts, the other solution is to coat and enclose the stent or stent struts with a soft, extremely elastic polymer and subsequently with a much harder and also more tear-proof polymer, wherein the leaflet is connected to the outer, comparatively harder layer. Alternatively, the gradual composite described can be applied first and on top of this harder up to softer layers are applied to which the leaflet is bound. The elastic layer between the harder base and the covering materials allows the adhesion and force transmission to be distributed over almost the entire area of the stent strut and therefore over a larger surface. Thus, stress peaks and possible detachment of the plastic are avoided or reduced, especially in areas where the leaflets are connected closest to the stent struts. This design is also particularly advantageous because softer formulations of a polymer, especially a polyurethane, exhibit better adhesion to other materials, especially metals, compared to formulations with a higher degree of hardness.

Preferably, only the distal crown has the composite structure made of several layers with different grades of hardness. This layered structure is also advantageous for materials other than the polyurethanes preferably used here.

As described previously, the valve stent is pre-treated and pre-coated. The cylindric wall of the valve stent, i.e. the mesh structure, is covered by a homogeneous (non-porous) or porous, permeable film or membrane. This surface layer or layers complete the membrane. A porous, especially fleece-like, fine-fibrillar structure is particularly suitable for the temporary folding of the valve stent to the small or very small diameter, which is required to place the valve into the lock of the catheter. The fleece-like, and hence fibrous, structure can be bent, folded or even creased into significantly smaller radii without damaging the membrane. This is especially advantageous for the relatively narrow gaps of the meshes and struts which are closer together or even touch each other after folding.

A further advantage of the fleece-like structure is that it seals the valve against the vessel or the annulus. If the cylindric wall is formed with a corresponding thickness, it can be used as sealing ring and will compensate for the differences in diameter between valve and vessel or the non-roundness of the vessel.

If the previously described anchoring stent is used, because it encloses the valve stent when installed, it can compensate for the gap between the anchoring stent and the valve stent. This facilitates the dimensioning or the correct size selection since the difference in the diameters between the anchoring or bulb stent, which is somewhat compressed by the vessel wall, and the valve stent, which is, if possible, completely expanded, is predictable and can be met by appropriate size diversity. Furthermore, surrounding cell or tissue structures can grow into the fleece from the vessel and thus contribute to the fixing of the valve. Another advantage of the fleece-like structure is that it is very well suited for gluing the valve in the vessel using a biocompatible glue, since the glue can penetrate the structure, thereby realizing a large contact area. In addition, this structure can be sewed very easily, so that the valve can be sewed in the vessel by threads or so-called (endo) clips, which are self-closing clips made of a memory alloy, or by means of other minimally invasive procedures. These fixing possibilities can be used alone or also in combination with the fixing hooks described earlier. For this, the microporous wall or surface layers are preferably connected only with the distal or valve-carrying crown elements or also partially with the proximal crown, if necessary. The folding is thus much gentler for the porous surface layers than if the surface layers are also fixed at the additional struts (the connection struts between distal and proximal crown). The surface layers thus create less resistance to the compression procedure (i.e. the folding). The struts can lie closer together and allow compression of the valve stent to a smaller diameter. The surface layers can be completely, partially or not at all connected to each other between the meshes. Furthermore, the surface layers can be completely, partially or not at all connected to the corresponding struts. The porous surface layers on both sides of the stent wall can be proximally extended beyond the proximal crown element and can be connected to each other only at their distal ends. Thus, the surface layers form pockets, which provide space for the folded stent expanding in an axial direction during the folding procedure. Therefore, it can be advantageous not to connect the surface layers at their proximal end to the proximal crown elements, or only partially to the "most proximal" region of the proximal crown elements.

The proximal ending of the surface layers can follow the course of the proximal waved crown element or lie in a circumferential direction forming a circle. At the distal end, the surface layer can also extend over the distal crown element and to some extent adopt the shape of the bulbs and commissures, as in a "stentless heart valve".

The valve stent, as well as the anchoring or bulb stents, can be coated with a surface layer having a fine-fibrillar structure, either on both sides or only on one side. When coated on both sides, one surface layer can also only partially cover the respective stent. Alternatively, especially the inner surface layer can also be a homogeneous film that does not have a porous or fine-fibrillar structure. A further alternative design intends that especially the inner side of the surface layers is a so-called laminated film, wherein especially the inner side facing the blood stream has the film and the other side of the laminated film has the porous, fine-fibrillar structure.

To connect the clamps to the fixing hooks, the surface layer must be opened or, if necessary, only partially covered at the outer side of the valve stent or, if necessary, of the anchoring stent. In this case, the surface layer must be cut open at least partially, so that the clamp or the connection element of the positioning wires can be fed through the surface layer to connect them to the fixing hooks using crimps or glue. For this purpose, the clamps should be previously straightened.

If the fixing hooks radially straighten or open their claws after releasing of the crimp connections, the fixing hooks can furthermore release a reservoir containing biocompatible glue, which can be used to adhere the surface layer to the vessel.

At least the outer surface layer of the stents is coated with a blood-compatible substance that is able to slide, so that the valve prosthesis can more easily be pushed out of the lock or again inserted into the lock. It is suitable to use highly water-absorbent polymers such as polyvinylpyrrolidone, polyvinyl alcohol or hydrogels. Valve leaflets that consist of a porous substance should also be coated with such or similar substances.

The valve leaflets are preferably attached along the distal crown, the connection line between stent and valve leaflet. They can be made of biological tissue (e.g. porcine valve leaflet, bovine pericardium or other tissue) or flexible plastic. In the following, polymer valve stents are preferably described. The leaflets can be produced as a homogeneous film (without porous structure) or made of a porous, permeable membrane. Thereby, the leaflets can also consist of several layers with different grades of hardness of the polymer. The pre-treatment and pre-coating of the stent, as described above, allows a particularly homogeneous transition between stent strut and leaflet to be achieved, so that a gradual opening can be achieved without narrow bending radii and with low stress as a whole.

The valve leaflets with porous structure, which here consist of a microporous, fine-fibrillar structure, are particularly advantageous for small venous valves, which need particularly soft leaflets for valve opening, and for erratically enlarging (growing with the body) valves in children. In these applications, especially good blood compatibility is much more important than in case of heart valve prostheses for adults, since the fatigue strength needed is not so high. Therefore, it is advantageous that surrounding cell structures can very easily grow in the fine-fibrillar structure and, therefore, with time can create a so-called neointima, which is extremely advantageous for blood compatibility. However, this growing-in procedure needs a certain amount of time, during which the risk of early-thrombotic or thromboembolic complications is increased. To reduce this risk, polymers that are especially blood-compatible, water-absorbent and thereby water-soluble or water-insoluble are embedded in or are coated on the porous structure. Representatives of these polymers are polyvinylpyrrolidone, polyvinyl alcohol, hydrogels (e.g. HEMA) or hydrogels based on polyethylene glycol. Hereby, especially biodegradable polymers can be used. It also makes sense to add to these polymers active substances that are antithrombogenic, antiproliferative or anti-inflammatory or possess other properties which improve blood- and biocompatibility of the prosthesis. Such active substances can be acetylsalicylic acid, heparin, rapamycin, tetrahydrocannabinol, siromilus, paclitaxel, zotarolimus, everolimus, cilostazol, pioglitazone or statins: e.g. cerivastatin, rosuvastatin or other active substances mentioned in the literature.

This combination of properties, made of a porous polymer matrix of preferably fine-fibrillar structure with incorporation of highly hydrophilic, preferably biodegradable or water-soluble polymers, which moreover can be used as drug carriers, is intended for all components of the percutaneous valve stent with a porous structure, in addition to its use for valve leaflets. Furthermore, it is of interest for a number of other applications, such as stitching rings for heart valve prostheses, artificial blood vessel prostheses, annuloplasty rings for reconstruction of mitral and tricuspid valves, stent grafts, as well as patches for diverse applications such as the treatment or covering of abdominal aortic aneurysms (AAA), or for use in endarterectomy of the carotid artery or other vessels, AV shunts or applications in the treatment of congenital heart defects, such as shielded patches to remedy defects of the septum or closure of the ductus artheriosus Botalli in cases of short-circuiting connections between the aorta and pulmonary artery.

All additional elements such as the anchoring stent and the bulb stent are preferably coated with a biocompatible polymer, the leaflet material, as is the valve stent. However, these stents can also be applied without coating.

In an alternative design, the bulb cage can also be completely covered, preferably with a fleece-like structure, so that the surrounding tissue and cell structures can grow into the porous membrane. In the design for the aortic position, the region where the ostia are arranged in the bulbs must, however, be open, to ensure the stream of blood into the coronary arteries. Respective, suitable designs of the bulb stent have already been described. Furthermore, the porous structures can be coated with hydrophilic polymers and active substances, as described for valve leaflets, to improve biocompatibility.

The previously described valve stents can also be used for integration into a conduit valve. As a strengthening element to absorb the clamp forces on the valve leaflets, they support the opening and closing movements due to their high flexibility. Thus, the design of the valve stent is preferably used for conduit valves, in which the proximal and distal crown elements run parallel or almost parallel to each other; that is, both crown elements have the same height.

In the design of a children's conduit valve prosthesis that must grow with the body, a conduit is preferably intended with formed bulbs made of the fleece-like, microporous and fine-fibrillar structure. The valve stent 13 as well as additional wireframes 131, located proximal to the valve stent 13 and distal to the bulbs 62, are integrated into the conduit (FIG. 13). These wireframes 131 are connected to the valve stent 13 via struts, if necessary, and are represented with reference signs 81, 81' as in FIG. 8.

As explained above for the covered valve stent, the valve stents can be covered by surface layers made of porous material on the outside or the inside of the wall or preferably on both sides. In contrast to the percutaneous design previously described, the surface layers, located on both sides of the stent, should be connected to each other between the meshes and also glued to the stent and all stent struts. The valve leaflets are preferably also made of the microporous, fine-fibrillar structure.

In addition, the porous structures can be coated with hydrophilic polymers and active substances to improve biocompatibility, as described for the valve leaflets.

The valve stents are preferably made of shape memory alloys, preferably nitinol, with a transformation temperature above body temperature. After production, the conduit is radially compacted or compressed up to a smaller diameter that is 50%, preferably only up to 70%, of its original diameter, at a temperature below the transformation temperature. After a respectively long implantation time, if the conduit valve has become too small for the growing organism, the temperature of the valve stent of the conduit valve should be increased above transformation temperature via an impulse, so that the valve stent can unfold to its original diameter. Even dependent on the tensioning capacity, the unfolding does not have to occur erratically but can also occur gradually, since the surrounding tissue or cell structures are grown into the porous structure, and these hinder erratic changes, and thus the transformation processes of these structures into the larger diameter occur gradually or require a certain amount of time. For the function of the conduit valves with diameters that change over time, valve stents made of the fleece-like structure are therefore preferable, since, due to the changes in diameter, these can better adapt to the deformation than a homogeneous material.

Further designs of this conduit valve prosthesis are possible. In particular, other stent structures than the one described here can also be integrated into the conduit. In addition, bulbs can be supported by stent structure types mentioned at the beginning using bulb stents. Moreover, it is advantageous to use valve stents of tapered conical shapes widened from proximal to distal, which approximate the geometry of the natural annulus. However, conically narrowing shapes can also be used for special cases.

The described conduit valve prosthesis can also be used as a normal conduit valve without additional stent structures upstream and downstream and without the property of erratic increase in size.

According to the invention, for production of a valve stent for uptake of polymeric valve leaflets with a 3D droplet dosing technology, a thin-walled sandwich structure with varying layer thickness and/or spatially varying degree of hardness is applied to the valve stent surface.

The 3D droplet dosing technology is a generative manufacturing process that allows the production of thin, sandwich-like membranes with locally varying layer thickness and composition, and spatially varying degree of hardness of a material type onto freeform surfaces. To achieve a defined thickness distribution of the thin membranes or films, individual drops of a polymeric solution or drops of a viscous polymerizing multi-component system are applied in a punctiform pattern, linearly in a row, in wavy lines or extensively onto the base body or a tool holder, the layer is then dried and the application of the drops is repeated until the desired, three dimensional polymeric body in the proper form is generated. For this purpose, accordingly suitable polymers are preferably dissolved in organic solvents to then process them in liquid form. Furthermore, preferably polyurethanes are used, which can dissolve very well in dimethylacetamide. However this solvent has a low vapour pressure, so that vaporization of the solvent takes a relatively long time. The drying temperature can only be increased within limits to avoid material damage. In addition, these polyurethanes are difficult to dissolve in solvents with high vapour pressure or are harder to process.

It is therefore intended to dissolve the polymer in a solvent mixture consisting of a high-boiling solvent and a second or, if necessary, third low-boiling solvent with high vapour pressure. Polyurethane, for example, can be dissolved in a solvent mixture consisting of dimethylacetamide and chloroform at a ratio between 20:80 and 90:10 (dimethylacetamide:chloroform), preferably within the range 35:65 to 70:30. For this purpose, it may be necessary to dissolve the polyurethane first in dimethylacetamide and only then add chloroform and mix the polymeric solution. With these ratios, the drying can be accelerated to such an extent that the polymers dries or freeze so quickly that the risk of dispersal on the tool holder is low, especially in case of 3 dimensional drying movements.

Usually, a certain excess in the diameter of the valve stent compared to the blood vessel is used to produce a radial pressure on the blood vessel by the prosthesis and thus improve the anchoring function. The blood vessel in turn applies pressure on the valve stent so that it cannot unfold completely and its function can be impaired. According to a further process variant, it is therefore intended that the valve leaflet is not adapted to the completely unfolded valve stent, but to a slightly compressed state which anticipates a middle reset of approximately 5-10% to 90-95% of the completely unfolded diameter, for example.

Therefore, the valve stent to be assembled on the tool holder is shrunken to this difference in diameter, and then the leaflets are attached. Following deformation, the valve stent unfolds, but only slightly, so that the leaflets as well as the wall, due to their elasticity, can adapt to this somewhat enlarged shape or the valve prosthesis is stored in this slightly shrunken state (in combination with a loading device to insert into the lock, if necessary).

The conventional surgically implantable prostheses, which are known, for example, from application DE 10050092A1, can be strengthened with an additional reinforcement ring in the base of the valve frame. For this purpose, it is appropriate to use a ring made of a shape memory alloy. Positioning or joining of the reinforced ring, which until now has been made of titanium or stainless steel, or of a frame in the same or similar shape as the valve stent, and the associated complete embedding in the composite structure, have so far been difficult. In addition, it involves the risk of the formation of bubbles if the production is carried out with dissolved polyurethanes.

Thus, it is proposed to use a ring made of a shape memory alloy, preferably nitinol, to expand it and align it on the tool holder, wherein the ring can easily slide over the coating because of its expanded shape. To a certain extent, the ring can also be pushed over protrusions caused by the tool holder. Subsequently, an increase of temperature above the shape transformation temperature of nitinol is carried out so that the ring contracts and is pressed onto the pre-coated tool holder and can be embedded. Thereafter, the ring is completely enclosed by application of one or more polyurethane layers.

The joining of valve, anchoring or bulb stent or of their fixing hooks to clamps or other fixing elements of the positioning wires is preferably carried out before packaging and sterilizing. The fixing hooks are therefore bent from a curved into a straight shape and are connected to each other in a force-locking manner by the clamps of the positioning wires using crimping pliers, for example. Alternatively or in addition, the clamps are directly connected to the fixing hooks or a strut of the stents. The clamps are made of a memory alloy with a shape transformation temperature above body temperature. Before packaging of the unit, the funnel-shaped applicator is also positioned so that the valve prosthesis or the catheter set is prepared for loading.

Before actual application of the percutaneous heart valve, the catheter head (that is, the not yet closed lock with the heart valve inside) is placed into water, so that the sliding layer that was applied at least externally, and was made of PVA or PVP for example, can absorb water and thus become able to slide. Furthermore, the valve prosthesis can be coated with active substances before application, for example by placing it in solutions. By pulling the positioning wires, the valve prosthesis is folded over the applicator and inserted into the lock and the lock head is closed. Preferably, a catheter system with lock head is used. The insertion of the valve prosthesis into the lock can also be carried out only by the withdrawal aid or using the coverings of the clamps.

After introduction of the guide wire via access vessels to the implantation site and beyond the implantation site and, if necessary, after the native leaflets are removed, the actual application process can start. This can be carried out in one step if the valve prosthesis to be applied consists only of the valve stent or of the valve stent and the anchoring or bulb stent connected to the valve stent. The application procedure is carried out in two steps if the anchoring or bulb stent is introduced first, followed by valve stent with valve leaflet.

In the one-step application of the heart valve catheter, it is guided by the guide wire to the implantation site, the lock head is opened and the valve stent is guided out using the positioning wires. The valve stent unfolds and is aligned and positioned at the implantation site via the positioning wires. Using imaging procedures, it is then checked if the valve stent is exactly located at the intended position in the annulus. If the valve stent is not precisely positioned, the valve stent will be re-positioned, wherefore, if necessary, the valve is again completely or partially withdrawn from the lock and is subsequently repositioned, until the valve stent is located at the precise position.

Subsequently, the clamps of the positioning wires are warmed up to their shape transformation temperature, which is above body temperature, using an electric current, a magnetic field or a laser, which has been used to remove the valve leaflets, so that the clamps open and the fixing hooks extend to their curved shape due to their intrinsic elasticity or their shape memory, and grip into the vessel wall and ultimately fix the valve stent. The positioning wires are withdrawn into the catheter and the catheter is removed from the body.

The fixing hooks can be made of the same shape memory alloy with the same shape transformation temperature as the valve stent, or of an alloy with a shape transformation temperature that is the same as the clamps, or preferably, of one with a shape transformation temperature above body temperature and below the shape transformation temperature of the clamps.

If the valve stent is made of a memory metal with a shape transformation temperature above body temperature, the valve stent must be warmed up to this shape transformation temperature to unfold after sliding out from the lock. The fixing hooks are thus preferably made of an alloy with a shape transformation temperature above the shape transformation temperature of the valve stent so that the valve stent or also the anchoring or bulb stent can still move and thus be positioned after extension and unfolding. The fixing hooks as well as the clamps are then warmed up to their shape transformation temperature, which is above the shape transformation temperature of the valve stent and above body temperature. By extension of the clamps, glue reservoirs can also be released, which adhere the valve to the annulus. The glue reservoirs are arranged in the wall of the valve stent between the porous surface layers or on the outer side of the wall. In the latter case, it can also simply be a surface layer that is arranged on the inner side of the valve stent.

The fixing hooks can also be a mandrel without a curved shape if the valve stent, as described, is alternatively adhered or sewed in a minimally invasively manner. The minimally invasive stitching is carried out using threads or self-closing clips ("endo clips"), which are stitched through the wall of the valve stent that is preferably made of a microporous, fine-fibrillar structure. A combination of fixing hooks and/or gluing and/or minimally invasive stitching can also be used. In particular, glue reservoirs can be released by extension of the fixing hooks, whereby the fine-fibrillar surface layer of the valve stent is glued to the vessel.

In an alternative approach, the connection between positioning wires and fixing hooks can be made of an additional, resoluble bonding which is, for example, redissolved by a high-frequency magnetic field following successful positioning of the valve at the implantation site.

Furthermore, there are possibilities other than clamps or gluing for the connection between the positioning wire and hooks or mandrel, such as micromechanical grippers. Alternatively, besides the force-locking connections, form-fitting connections are also intended. Especially for a form-fitting connection, additional holding or guidance points are arranged, which have no other function. The form-fitting connections can also be connected only with the struts of the stent.

In the two-step application, the anchoring stent or the bulb stent is first applied as described previously for the valve stent. The bulb stent can thereby also be used in a design option without fixing hooks or extending claws since, due to the strong expansion of the annulus, the bulb stent is sufficiently anchored without fixing hooks.

Subsequently, the valve stent is applied. For this, the lock is guided to the implantation site, the valve stent is at least partially guided out from the lock and oriented and positioned with respect to the anchoring or bulb stent so that the valve stent is positioned within the anchoring or bulb stent and the bayonet-like lock can grip. Alternatively or additionally, the clamps can then be redissolved in the manner described above, so that the fixing hooks can grip the anchoring or bulb stent and/or also be fixed in the annulus or vessel.

The previously described procedures preferably relate to self-expanding valve, anchoring or bulb stents. However, in principle it is also possible that these stents, preferably only anchoring stents or bulb stents, are not self-expanding stents. In this case, the stents should be expanded at the implantation site using a balloon catheter. In the case of the bulb stent, the balloon catheters are adapted to the shape of the bulb stent. The above also applies to the application of the valve prosthesis via glue pipes.

The application of a percutaneous valve prosthesis using glue pipes can be carried out alternatively or in additional to the previous application via positioning wires.

The joining or connection of valve or anchoring stents to glue pipes is preferably carried out before packaging and sterilizing. The glue pipes are guided via loops on the covering (that is, the surface layers of the stent) or they are pulled directly through the fine-fibrillar structure. Additional, self-opening clips or clamps, which fix the pipes preferably to the connection struts of the stent, also function as a lock for the glue pipes and are made of a memory alloy with a shape transformation temperature above body temperature. A funnel-shaped applicator is also positioned prior to packaging of the unit, so that the valve prosthesis or the catheter set is prepared for loading.

Before the actual application of the percutaneous heart valve, the catheter head (that is, preferably the not yet closed lock with the heart valve inside) is placed into water so that so that the sliding layer that was applied at least externally and made of PVA or PVP, for example, can absorb water and thus becomes able to slide. Furthermore, the valve prosthesis can be coated with active substances before application, by placing in solutions, for example.

By pulling the glue pipes or additional positioning wires, if existent, the valve prosthesis is then folded using the applicator and inserted into the lock and the lock head is closed. Preferably, a catheter system with lock head is used. The introduction of the valve prosthesis into the lock can also be carried out by the withdrawal aid alone or using the coverings of the clamps.

After introduction of the guide wire via access vessels to the implantation site and beyond the implantation site and, if necessary, after the native leaflets are removed, the actual application process can start. This can be carried out in one step if the valve prosthesis to be applied consists only of the valve stent or of the valve stent and the anchoring or bulb stent connected to the valve stent. The application procedure is carried out in two steps if the anchoring or bulb stent are introduced first, followed by valve stent with valve leaflet.

In the one-step application, the heart valve catheter is guided by the guide wire to the implantation site, the lock head is opened and the valve stent is guided out using the glue pipes or additional positioning wires, if existent. The valve (consisting of the valve stent with valve or, if necessary, additionally connected to the bulb or anchoring stent) unfolds and is aligned and positioned at the implantation site via the glue pipes. Using imaging procedures, it is checked if the valve is located as exactly as possible at the intended position in the vessel or the annulus. If the valve stent is not precisely positioned, the valve will be re-positioned, wherefore, if necessary, the valve is again completely or partially withdrawn from the lock and is subsequently repositioned, until the valve is located at the precise position. Subsequently, the clamps of the positioning wires are warmed up to their shape transformation temperature, which is above body temperature, using the known methods, so that the clips and glue pipes open and can be moved. It will be particularly advantageous if, in this step of the procedure, the fixing hooks situated at the valve stent are additionally extended by warming them up to their shape transformation temperature which is above body temperature. The fixing hooks grip into the vessel wall and fix the valve for the further procedure without migration of the valve prosthesis. Because the clip is opened, the supply of glue is activated. The glue pipes are slowly pulled back via the loops along the valve stent base and into the catheter while glue continually leaks and glues the valve stent base to the vessel wall. The catheter is finally removed from the body.

If the valve stent is made of a memory metal with a shape transformation temperature above body temperature, the valve stent must be warmed up to this shape transformation temperature to unfold after withdrawal from the lock. The fixing hooks are then preferably made of an alloy with a shape transformation temperature above the shape transformation temperature of the valve stent to allow the valve stent or also the anchoring or bulb stent to be moved and thus positioned after extension and unfolding. The fixing hooks as well as the clamps are then warmed up to their shape transformation temperature, which is above the shape transformation temperature of the valve stent and above body temperature.

The application of the valve via glue pipes and the gluing of the valve can also be carried out in combination with the hooks or by minimally invasive stitching.

In an alternative approach, the connection between positioning wires and fixing hooks or mandrels can also be made of an additional, soluble bonding which is, for example, redissolved by a high-frequency magnetic field following successful positioning of the valve at the implantation site.

In the two-step application, the anchoring stent or the bulb stent is first applied as described previously for the valve stent. The bulb stent can thereby be used in a design option without fixing hooks or extending claws since the bulb stent is sufficiently anchored without fixing hooks, as a result of the strong expansion of the annulus.

Subsequently, the valve stent is applied. Therefore, the lock is guided to the implantation site, the valve stent is at least partially withdrawn from the lock and oriented and positioned with respect to the anchoring or bulb stent so that the valve stent is positioned within the anchoring stent or bulb stent and the bayonet-like lock can grip. This is also not required in this process variant, since the valve stent can also be glued to the anchoring or bulb stent.

Alternatively or additionally, the clamps can then be redissolved in the manner described above, so that the fixing hooks can grip the anchoring or bulb stent and/or also fix it in the annulus or vessel.

The valve stent integrated into the conduit and the proximal and distal stent regions are made of a shape memory alloy with a shape transformation temperature above body temperature. Prior to packaging and sterilization or at least prior to implantation, the valve conduit is compressed to the desired smaller diameter, which is preferably approximately 70-95% of the completely unfolded conduit. Shortly before or during implantation, the conduit is then, if necessary, adjusted to the recipient organism by trimming its proximal and/or distal ends.

If the valve conduit has become too small for the growing recipient organism, the valve conduit or the integrated stents are warmed to a temperature above their shape transformation temperature so that the valve conduit can be unfolded gradually and increases in its diameter and within limits can be adapted to the growing organism. The warming up can be carried out by a high-frequency magnetic field, for example. Another possibility is to warm it up by electric current, which can be transmitted in a minimally invasive manner via a catheter to the stents of the valve conduit.

The application of a percutaneous valve prosthesis that is in an intermediary or partly unfolded state is basically carried out exactly as described above for a percutaneous valve prosthesis. If the heart valve in a child becomes too small for the growing recipient organism or the venous valve becomes too small due to the dilatation of the vein, the child heart valve or the venous valve or the stents integrated therein are warmed up to the shape transformation temperature of the valve stent device that previously inhibited the complete unfolding of the valve stent or also the bulb stent, so that the child heart valve or the venous valve can gradually unfold and increase in diameter.

According to the prior art, it is known that stents, which are small wireframes in a tube form made of metal, are produced by laser cutting. The semi-finished products for manufacturing of the stents are tubes made of metal, wherein stainless steel alloys or shape memory alloys such as nitinol, for example, are mostly used. Stents with relatively large diameter (approximately >10 mm) in operative state are frequently made of stent tubes with small diameter and subsequently transferred to the operative state, i.e. the expanded state, using transforming or heat-treating processes. Especially in the case of nitinol, only tubes with a relatively small diameter up to approximately 10 mm have been available on the market as semi-finished products until now. This is based on costs and because it is difficult and costly to draw tubes with only a few tenths of a millimeter wall thickness to larger diameters and to produce them in exact dimensions and tolerances.

Therefore, according to a preferred design of the process according to the invention, it is intended that the valve stent is first cut from a tube with a smaller diameter, wherein the bar thickness is produced with an excess, and is then expanded to the desired diameter and cut exactly to size.

It is difficult to calculate in advance the exact stent geometry in the manufacturing state with a much smaller diameter from its operative state with a large diameter (i.e. the expanded final state). As long as there are only small differences between the suggested and the actual stent geometry, this is not a problem for conventional, mesh-like stents for vessels, since only bar thickness, wall thickness and diameter are important.

For percutaneous heart valves, however, in particular for those with polymeric valve leaflets, it is important to calculate exactly the geometry of the stent in its functional state and in its operative state, the state with the large diameter. The wall thickness of the stent corresponds to that of the final tube as much as possible. Now the stent is expanded to a tube with the suggested diameter for the functional state and, in a second step, is cut exactly to size. Between expansion of the stent and the re-cutting in the second step, or also only after this step, the stent is subjected to appropriate transforming or, if necessary, heat-treating processes to transfer it to its operative state, i.e. the expanded state, or to fix it.

The approximate valve stent geometry in the manufacturing state is calculated in advance using FEM analysis, and the bar thickness is produced with an excess in relation to the calculated geometry.

It should be noted that for this process, the stent could have a larger wall thickness in the manufacturing state than in the expanded state (operative state). The stent would subsequently be re-worked to its final wall thickness using suitable procedures such as grinding.

Anchoring and valve stents can be produced similarly. For bulb stents, the design of the bulbs can be carried out after the initial pre-cutting of the stent frame. The transforming and heat-treating processes must be carried out after shaping the bulbs or only after the re-cutting.

To produce a percutaneous heart valve, a venous valve or a heart valve for a child, the stent is cut or lasered at 20° C. to 37° C., and subsequently, the hooks are welded on at 40° C. to 60° C. For pre-treatment of the stent, there can be an improvement of adhesion, if necessary, and repeated coating via immersion or if necessary by 3D droplet dosing technology with subsequent drying at 60° C., for example (for 3D technology, compare, for example, DE10050305A1). Using a tool holder as a valve stent moulding tool, a fleece can be applied by spraying using a deformation aid as well as a separating layer, if necessary, wherein, depending on whether the fleece is to be applied later as leaflet material or as a film, the leaflet region is protected during the spray application.

The pre-treated stent is then oriented along the leaflet attaching line, wherefore it is previously cooled, if necessary, and slightly expanded, so that, due to its shape memory, the stent can be slid over the tool and the fleece layer deposited on it without damage. Following an appropriate increase in the temperature, the stent is fixed on the holding tool. By dosing of thin lanes along the stent struts using the known 3D droplet dosing technology, preferably along the leaflet attaching line, the stent can be fixed at the fleece layer (as sheathing for the stent struts). The struts or the regions of the inner surface layer which should not be connected to the outer surface layer are covered with a separating agent such as PVA or PVP, which can be inlaid as separating film or applied by 3D droplet coating. The valve leaflets can be a fleece prepared as a film. A leaflet fleece is preferred for venous valves since a lower thrombogenicity is expected as a result of improved cell ingrowth. The leaflet film features a longer shelf-life and is therefore preferable for percutaneous heart valves.

If a second layer is to be sprayed on to produce a porous stent wall, the existing hooks must previously be fixed using clamps, if necessary, and the hooks and the leaflet, if it is made of a film, must be protected in advance using separating aids. If necessary, valve leaflets can also have several layers applied using the 3D droplet dosing technology, known in principle, and with respective intermediate drying. The free leaflet edges and the surface layers of the valve stent along the proximal ends are cut, the existing separation film is removed, if necessary, and the outer surface layer is partially cut open to uncover the hooks and partially connect them to clamps. The proximal ends of the surface layers are closed, preferably by gluing; if necessary, a glue reservoir must be created. Separating agents that may have been used in advance, such as PVA/PVP, can be dissolved in water to separate surface layers from struts. For the production of valves for children, after cutting the free leaflet edges and the application of the stent to the moulding tool, a conduit is generated by spraying and by subsequently proximately and distally cutting.

To improve biocompatibility, porous structures can be coated with hydrophilic polymers and/or other active agents.

The production of an anchoring stent or a bulb stent is carried out analogously (as described above), with possible surface layers made of fleece or a bulb applied by spraying. Connections of the anchoring stent to the valve stent can be generated with threads, by gluing or common surface layers.

To produce a surgically implantable aortic or mitral valve prosthesis with a reinforced metallic base ring, a ring made of memory metal is used to avoid formation of bubbles. The ring is expanded, positioned on the coated holding tool, oriented and subsequently fixed using the memory effect, before the final coating with a polymer is carried out to enclose and embed the ring completely.

The invention claimed is:

1. A valve stent comprising:
a proximal crown element comprising no more than three u-shaped proximal crown element bends, each of said u-shaped proximal crown element bends comprising a crown element base and two crown element end portions, each of said two crown element end portions defining a distal-most portion of one of said u-shaped crown element bends, said base defining a proximal-most portion of said one of said u-shaped crown element bends, said crown element base being located between said two crown element end portions;
a distal crown element comprising no more than three u-shaped distal crown element bends, wherein a shape of one of said u-shaped distal crown element bends is different from a shape of one of said proximal u-shaped crown element bends, wherein said proximal crown element is flatter than said distal crown element, said u-shaped distal crown element bend comprising two distal crown element end portions and a distal crown element base, each of said two distal crown element end portions defining a distal-most portion of said distal crown element, said distal crown element base defining a proximal-most portion of said distal crown element, said distal crown element base being located between said two distal crown element end portions, said proximal crown element and said distal crown element being arranged coaxially one behind the other, wherein ends of said proximal crown element and said distal crown element are arranged directly successive and are not distorted by an angle, each of said u-shaped distal crown element bends being connected directly with one valve leaflet; and
connecting bars, each of said connecting bars extending exclusively from one proximal crown element base to one of said distal crown element end portions.

2. A valve stent, according to claim 1, wherein at least one of the proximal crown element and the distal crown element comprise two or three u-shaped bends connected to each other at the ends.

3. A valve stent, according to claim 1, wherein the proximal crown element and the distal crown element arranged one behind the other form the valve stent, said connecting bars being directly connected to said bases of said proximal crown element and said ends of said distal crown element, said u-shaped distal crown element bend and at least one of said u-shaped crown element bends face in a same direction.

4. A valve stent, according to claim 1, wherein each of the proximal crown element and the distal crown element comprise bars and the connecting bars are wider than the bars of the crown elements.

5. A valve stent, according to claim 1, wherein the valve stent is self-expanding, wherein the valve stent in a folded state takes an expanded shape due to an elasticity thereof and/or a shape memory thereof.

6. A valve stent, according to claim 1, wherein the valve stent flares conically from a proximal to a distal end.

7. A valve stent, according to claim 1, further comprising fixing hooks griping into a natural vessel wall.

8. A valve stent, according to claim 7, wherein the fixing hooks are arranged at the base of the distal crown element and are oriented against the flow direction.

9. A valve stent, according to claim 7, wherein the fixing hooks are arranged at distal ends of said proximal crown element and are oriented with a flow direction.

10. A valve stent, according to claim 7, wherein the fixing hooks are made of the same material as the valve stent.

11. A valve stent, according to claim 7, wherein the fixing hooks are made of a shape memory alloy and are straight during transdermal application of the valve stent.

12. A valve stent, according to claim 1, further comprising flexible wires fixed with free ends to two adjacent connection bars.

13. A valve stent, according to claim 12, further comprising clamps, wherein the flexible wires are fixed with the clamps to the connection struts, wherein the clamps and/or the wires are made of a shape memory metal.

14. A valve stent, according to claim 1, further comprising a separate anchoring stent having at least one or more than one crown elements wherein the separate anchoring stent can be placed between the crown elements of the valve stent so that the separate anchoring stent is positioned within the valve stent.

15. A valve stent, according to claim 14, wherein the separate anchoring stent deviates from a circular cylindrical shape.

16. A valve stent, according to claim 14, wherein the separate anchoring stent can be connected to the valve stent via radial expansion of the valve stent.

17. A valve stent, according to claim 1, further comprising a bulb stent that forms artificial bulbs that widen a vessel in a bulb-shaped manner.

18. A valve stent, according to claim 17, wherein cross-shaped stent struts each form one bulb.

19. A valve stent, according to claim 17, further comprising another bulb stent to provide two bulb stents wherein the two bulb stents are axially offset to each other so that the two bulb stents form a diamond-shaped opening in a region of crossing points.

20. A valve stent, according to claim 17, further comprising another bulb stent to provide a plurality of bulbs wherein struts running in an axial direction form the bulbs.

21. A valve stent, according to claim 17, wherein the bulb stent is connected to the valve stent, wherein the bulb stent and the connection strut of the valve stent are connected by threads or the bulb stent and the valve stent are welded or glued at points.

22. A valve stent, according to claim 1, further comprising:
fixing hooks; and
a separate anchoring stent having a crown element wherein the separate anchoring stent can be placed between the crown elements of the valve stent so that the separate anchoring stent is positioned within the valve stent and wherein the fixing hooks of the valve stent grab into the anchoring stent.

23. A valve stent, according to claim 1, wherein the valve stent is coated with a coating material, which exhibits hardenings preferably increasing or decreasing from the inside to the outside or hardenings at first increasing and then decreasing.

24. A valve stent, according to claim 23, wherein the coating material is a hyperbranched polymer or a base polymer for silanised polymers.

25. A valve stent, according to claim 23, wherein the stent struts are successively coated with plastics with a decreasing degree of hardness.

26. A valve stent, according to claim 23, wherein the stent struts are first coated with a soft polymer and subsequently with a comparatively harder polymer, wherein the leaflet is connected to the outer, comparatively harder layer.

27. A valve stent, according to claim 1, wherein each of said u-shaped bends is connected to one of said two distal crown element end portions via only one of said connecting bars and to another one of said two distal crown element end portions via only another one of said connecting bars, said one of said two distal crown element end portions being adjacent to said another one of said two distal crown element end portions.

28. A valve stent according to claim 1, wherein each said proximal crown element base is connected directly to two adjacent ends of said distal crown element.

29. A valve stent comprising:
a plurality of crown elements arranged coaxially one behind the other, said plurality of crown elements comprising a proximal crown element and a distal crown element, said distal crown element being formed by no more than three distal crown u-shaped bends, each of said distal crown u-shaped bends comprising a distal crown base and two distal crown ends, said distal crown base defining a proximal-most portion of one of said distal crown u-shaped bends, each of said two distal crown ends defining a distal-most portion of said one of said distal crown u-shaped bends, said proximal crown element comprising no more than three proximal crown u-shaped bends, said proximal crown u-shaped bends having a shape that is different from a shape of said distal crown u-shaped bends, wherein said proximal crown element is flatter than said distal crown element, each of said proximal crown u-shaped bends comprising a proximal crown base and two proximal crown ends, said proximal crown base defining a proximal-most portion of one of said proximal crown u-shaped bends, said two proximal crown ends defining a distal-most portion of said one of said proximal crown u-shaped bends, wherein ends of said proximal crown element and said distal crown element are arranged directly successive and are not distorted by an angle, each of said distal crown u-shaped bends being directly connected to one valve leaflet; and
a plurality of connecting bars, one of said plurality of connecting bars engaging said proximal crown base of one of said proximal crown u-shaped bends and said distal crown element, another one of said plurality of connecting bars engaging said proximal crown base of another one of said proximal crown u-shaped bends and said distal crown element, wherein each of said connecting bars extends from one of said proximal crown u-shaped bends to one of said two distal crown ends.

30. A valve stent according to claim 29, wherein each said proximal crown element base is connected directly to said two distal crown ends, said two distal crown ends being adjacent to each other.

31. A valve stent according to claim 29, wherein the crown elements arranged one behind the other form the valve stent, said distal crown base facing said proximal crown base, said distal crown base being directly opposite said proximal crown base with respect to a longitudinal axis of said distal crown element and a longitudinal axis of said proximal crown element.

32. A valve stent according to claim 29, wherein each of the crown elements comprise bars and the connecting bars are wider than the bars of the crown elements.

33. A valve stent according to claim 29, wherein each of said distal crown u-shaped bend and each of said proximal crown u-shaped bends face in a same direction, wherein each of said distal crown u-shaped bends is located directly opposite one of said proximal crown u-shaped bends with respect to a longitudinal axis of said distal crown element and said proximal crown element.

34. A valve stent according to claim 33, wherein at least a portion of said one of said plurality of connecting bars and at least a portion of said another one of said plurality of connecting bars are located between said two proximal crown ends and said two distal crown ends.

35. A valve stent according to claim 29, wherein each of said proximal crown u-shaped bends is connected to one of said distal crown ends via only one of said connecting bars and to another one of said distal crown ends via only another one of said connecting bars, said one of said two distal crown ends being located adjacent to said another one of said distal crown ends.

36. A valve stent comprising:
a first u-shaped bent element having a first u-shaped bent element end portion;
a second u-shaped bent element having a second u-shaped bent element end portion, said first u-shaped bent element end portion being connected to said second u-shaped bent element end portion, wherein at least said first u-shaped bent element end portion and said second u-shaped bent element end portion define a distal crown element wherein the distal crown element is formed by no more than three u-shaped bent elements, said first u-shaped bent element end portion and said second u-shaped bent element end portion defining a distal-most portion of the stent, each of said first u-shaped bent element and said second u-shaped bent element being directly connected with one valve leaflet;
a third u-shaped bent element having a third u-shaped bent element first end portion, a third u-shaped bent element second end portion and a third u-shaped element base portion, said third u-shaped element base portion being located between said third u-shaped bent element first end portion and said third u-shaped bent element second end portion;
a fourth u-shaped bent element having a fourth u-shaped bent element first end portion, a fourth u-shaped bent element second end portion and a fourth u-shaped element base portion, said fourth u-shaped element base portion being located between said fourth u-shaped bent element first end portion and said fourth u-shaped bent element second end portion, said fourth u-shaped bent element first end portion being connected to said third-shaped bent element first end portion, wherein at least said fourth u-shaped bent element first end portion and said third u-shaped bent element first end portion define a proximal crown element wherein the proximal crown element is formed by no more than three u-shaped bent elements, wherein a shape of said fourth u-shaped bent element and a shape of said third u-shaped bent element are different from a shape of said first u-shaped bent element and a shape of said second u-shaped bent element, wherein said third and fourth u-shaped bent elements are flatter than said first and second u-shaped bent elements, said distal crown element being arranged opposite said proximal crown element, said third u-shaped element base portion and said fourth u-shaped element base portion defining a proximal-most portion of the stent, wherein said fourth u-shaped bent element end portion and said third u-shaped bent element end portion are located between said first u-shaped bent element and said second u-shaped bent element;
a first connecting bar connected to said third u-shaped bent element and at least said first u-shaped bent element, wherein said first connecting bar is in direct contact with at least said third u-shaped element base portion;
a second connecting bar connected to said fourth u-shaped bent element and at least said second u-shaped bent element, wherein said second connecting bar is in direct contact with at least said fourth u-shaped element base portion, said first connecting bar and said second connecting bar extending exclusively between said distal-most portion of the stent and said proximal-most portion of the stent.

37. A valve stent according to claim 36, wherein said first connecting bar is in direct contact with at least said first u-shaped bent end portion and said second connecting bar is in direct contact with at least said second u-shaped bent end portion, each of the crown elements comprising bars and the first connecting bar and the second connecting bar being wider than the bars of the crown elements, wherein ends of said proximal crown element and said distal crown element are arranged directly successive and are not distorted by an angle.

38. A valve stent according to claim 37, wherein said first connecting bar extends exclusively between said third u-shaped element base portion and said distal crown element, said second connecting bar extending exclusively between said fourth u-shaped element base portion and said distal crown element.

39. A valve stent according to claim 36, wherein said first u-shaped bent element comprises a first u-shaped bent element base portion, said second u-shaped bent element comprising a second u-shaped bent element base portion, wherein at least a portion of said first connecting bar extends between said first u-shaped bent element base portion and said third u-shaped bent element base portion, at least a portion of said second connecting bar extending between said second u-shaped bent element base portion and said fourth u-shaped bent element base portion, said first u-shaped bent element end portion and said second u-shaped bent element end portion being located directly opposite said fourth u-shaped bent element first end portion and said third-shaped bent element first end portion with respect to a longitudinal axis of the stent.

* * * * *